United States Patent [19]

Thompson et al.

[11] Patent Number: 5,143,829

[45] Date of Patent: Sep. 1, 1992

[54] HIGH LEVEL EXPRESSION OF BASIC FIBROBLAST GROWTH FACTOR HAVING A HOMOGENEOUS N-TERMINUS

[75] Inventors: Stewart A. Thompson, Mountain View; Judith A. Abraham, Sunnyvale, both of Calif.

[73] Assignee: California Biotechnology Inc., Mountain View, Calif.

[21] Appl. No.: 501,206

[22] Filed: Mar. 29, 1990

[51] Int. Cl.[5] .................. C12N 1/21; C12N 15/18; C12N 15/00
[52] U.S. Cl. .................. 435/69.4; 530/399; 435/320.1; 435/240.2; 435/252.33; 435/252.3
[58] Field of Search ............ 435/252.33, 252.3, 320.1, 435/240.2, 69.4; 536/27; 530/399

[56] References Cited

PUBLICATIONS

Abraham, J. et al., Science (1986) 233:545–548.
Abraham, J. et al., The EMBO Journal (1986) 5(10):2523–2528.
Florkiewicz, R. and Sommer, A., PNAS USA (1989) 86:3978–3981.
Prats, H. et al., PNAS USA (1989) 86:1836–1840.
Barr, P. et al., J. Biol. Chem. (1988) 263(31):16471–16478.
Iwane et al., BBRC (1987) 146(2):470–477.
Squires et al., J. Biol. Chem. (1988) 263(31):16297–16302.
Fox et al., J. Biol Chem. (1988) 263(34):18452–18458.

Primary Examiner—David L. Lacey
Assistant Examiner—Marianne Porta Allen
Attorney, Agent, or Firm—Peter R. Shearer

[57] ABSTRACT

DNA sequences are provided which encode a form of basic fibroblast growth factor lacking one of the alanine residues immediately following the N-terminal methionine residue of the primary translation product. The DNA sequences can be expressed to produce basic fibroblast growth factor having a homogeneous N-terminus.

11 Claims, 21 Drawing Sheets

```
      1                   5                        10                        15
    Met Ala Ala Gly Ser Ile Thr Thr Leu Pro Ala Leu Pro Glu Asp Gly Gly Ser
    ATG GCA GCC GGG AGC ATC ACC ACG CTG CCC GCC TTG CCC GAG GAT GGC GGC AGC
    -9                                          -1  1

20                        25                        30                        35
    Gly Ala Phe Pro Pro Gly His Phe Lys Asp Pro Lys Arg Leu Tyr Cys Lys Asn
    GGC GCC TTC CCG CCC GGC CAC TTC AAG GAC CCC AAG CGG CTG TAC TGC AAA AAC
    10                                        20

40                        45                        50
    Gly Gly Phe Phe Leu Arg Ile His Pro Asp Gly Arg Val Asp Gly Val Arg Glu
    GGG GGC TTC TTC CTG CGC ATC CAC CCC GAC GGC CGA GTT GAC GGG GTC CGG GAG
                  30                                        40

55                        60                        65                        70
    Lys Ser Asp Pro His Ile Lys Leu Gln Leu Gln Ala Glu Glu Arg Gly Val Val
    AAG AGC GAC CCT CAC ATC AAG CTA CAA CTT CAA GCA GAA GAG AGA GGA GTT GTG
                              50                                        60

75                        80                        85                        90
    Ser Ile Lys Gly Val Cys Ala Asn Arg Tyr Leu Ala Met Lys Glu Asp Gly Arg
    TCT ATC AAA GGA GTG TGT GCT AAC CGT TAC CTG GCT ATG AAG GAA GAT GGA AGA
                              70                                        80

95                        100                       105
    Leu Leu Ala Ser Lys Cys Val Thr Asp Glu Cys Phe Phe Phe Glu Arg Leu Glu
    TTA CTG GCT TCT AAA TGT GTT ACG GAT GAG TGT TTC TTT TTT GAA CGA TTG GAA
                                          90

110                       115                       120                       125
    Ser Asn Asn Tyr Asn Thr Tyr Arg Ser Arg Lys Tyr Thr Ser Trp Tyr Val Ala
    TCT AAT AAC TAC AAT ACT TAC CGG TCA AGG AAA TAC ACC AGT TGG TAT GTG GCA
    100                                       110

FIG.1A-1
```

```
                              130                              135                         140
Leu Lys Arg Thr Gly Gln Tyr Lys Leu Gly Ser Lys Thr Gly Pro Gly Gln Lys
TTG AAA CGA ACT GGG CAG TAT AAA CTT GGA TCC AAA ACA GGA CCT GGG CAG AAA
        120                                          130

145                        150                        155
Ala Ile Leu Phe Leu Pro Met Ser Ala Lys Ser
GCT ATA CTT TTT CTT CCA ATG TCT GCT AAG AGC TGA
        140                                    146
```

FIG.1A-2

```
  1
  Met Ala Ala Gly Ser Ile Thr Thr Leu Pro Ala Leu Pro Glu Asp Gly Gly Ser
  ATG GCC GCC GGG AGC ATC ACC ACG CTG CCA GCC CTG CCG GAG GAC GGC GGC AGC      54

20                          25                          30                          35
  Gly Ala Phe Pro Pro Gly His Phe Lys Asp Pro Lys Arg Leu Tyr Cys Lys Asn
  GGC GCT TTC CCG CCG GGC CAC TTC AAG GAC CCC AAG CGG CTG TAC TGC AAG AAC     108

40                          45                          50
  Gly Gly Phe Phe Leu Arg Ile His Pro Asp Gly Arg Val Asp Gly Val Arg Glu
  GGG GGC TTC TTC CTG CGC ATC CAC CCC GAC GGC CGA GTG GAC GGG GTC CGC GAG     162

55                          60                          65                          70
  Lys Ser Asp Pro His Ile Lys Leu Gln Leu Gln Ala Glu Glu Arg Gly Val Val
  AAG AGC GAC CCA CAC ATC AAA CTA CAA CTT CAA GCA GAA GAG AGA GGA GTT GTG     216

Ser Ile Lys Gly Val Cys Ala Asn Arg Tyr Leu Ala Met Lys Glu Asp Gly Arg
  TCT ATC AAA GGA GTG TGT GCT AAC CGT TAC CTG GCT ATG AAA GAA GAT GGA AGA     270

95                         100                         105
  Leu Leu Ala Ser Lys Cys Val Thr Asp Glu Cys Phe Phe Phe Glu Arg Leu Glu
  TTA CTA GCT TCT AAA TGT GTT ACA GAC GAG TGT TTC TTT TTT GAA CGA TTG GAG     324

110                         115                         120                         125
  Ser Asn Asn Tyr Asn Thr Tyr Arg Ser Arg Lys Tyr Ser Ser Trp Tyr Val Ala
  TCT AAT AAC TAC AAT ACT TAC CGG TCA AGG AAA TAC TCC AGT TGG TAT GTG GCA     378

130                         135                         140
  Leu Lys Arg Thr Gly Gln Tyr Lys Leu Gly Pro Lys Thr Gly Pro Gly Gln Lys
  CTG AAA CGA ACT GGG CAG TAT AAA CTT GGA CCC AAA ACA GGA CCT GGG CAG AAA     432
```

FIG.1B-1

```
145                 150                     155
Ala Ile Leu Phe Leu Pro Met Ser Ala Lys Ser
GCT ATA CTT TTT CTT CCA ATG TCT GCT AAG AGC TGA TCTTAATGGC AGCATCTGAT   488

CTCATTTTAC ATGAAGAGGT ATATTTCAGA AATGTGTTAA   528
```

FIG.1B-2

```
     1                     5                    10                    15
     Met Ala Gly Ser Ile Thr Thr Leu Pro Ala Leu Pro Glu Asp Gly Gly Ser      54
     CAT ATG GCT GGT TCT ATC ACT ACC CTG CCA GCT CTG CCA GAA GAC GGT GGT TCT
     NdeI 20                    25                    30                    35
     Gly Ala Phe Pro Pro Gly His Phe Lys Asp Pro Lys Arg Leu Tyr Cys Lys Asn     108
     GGT GCC TTC CCA CCA GGT CAC TTC AAA GAC CCA AAA CGT CTG TAC TGC AAA AAC 40                    45                    50
     Gly Gly Phe Phe Leu Arg Ile His Pro Asp Gly Arg Val Asp Gly Val Arg Glu    162
     GGT GGT TTC TTC CTG CGC ATC CAC CCC GAC GGC CGA GTG GAC GGG GTC CGC GAG
                        HhaI 55                    60                    65                    70
     Lys Ser Asp Pro His Ile Lys Leu Gln Leu Gln Ala Glu Glu Arg Gly Val Val    216
     AAG AGC GAC CAC ATC AAA CTA CAA CTT CAA GCA GAA GAG AGA GGG GTT GTG 75                    80                    85
     Ser Ile Lys Gly Val Cys Ala Asn Arg Tyr Leu Ala Met Lys Glu Asp Gly Arg    270
     TCT ATC AAA GGA GTG TGT GCA AAC CGT TAC CTT GCT ATG AAA GAA GAT GGA AGA 90                    95                   100                   105
     Leu Leu Ala Ser Lys Cys Val Thr Asp Glu Cys Phe Phe Phe Glu Arg Leu Glu    324
     TTA CTA GCT TCT AAA TGT GTT ACA GAC GAG TGT TTC TTT TTT GAA CGA TTG GAG 110                   115                   120                   125
     Ser Asn Asn Tyr Asn Thr Tyr Arg Ser Arg Lys Tyr Thr Ser Trp Tyr Val Ala    378
     TCT AAT AAC TAC AAT ACT TAC CGG TCA AGG AAA TAC ACC AGT TGG TAT GTG GCA
```

FIG.2-1

```
                    130                        135                        140
Leu Lys Arg Thr Gly Gln Tyr Lys Leu Gly Ser Lys Thr Gly Pro Gly Gln Lys
CTG AAA CGA ACT GGG CAG TAT AAA CTT GGA TCC AAA ACA GGA CCT GGG CAG AAA    432

145                        150                    154
Ala Ile Leu Phe Leu Pro Met Ser Ala Lys Ser
GCT ATA CTT TTT CTT CCA ATG TCT GCT AAG AGC TGA TCTTAATGGC AGCATCTGAT      488

CTCATTTTAC ATGAAGCTT                                                       507
           HindIII
```

FIG.2-2

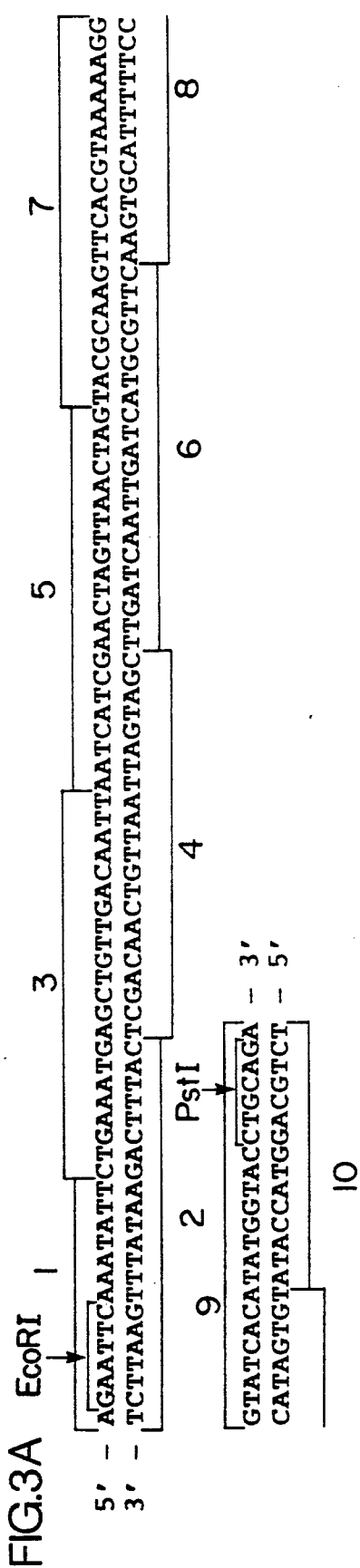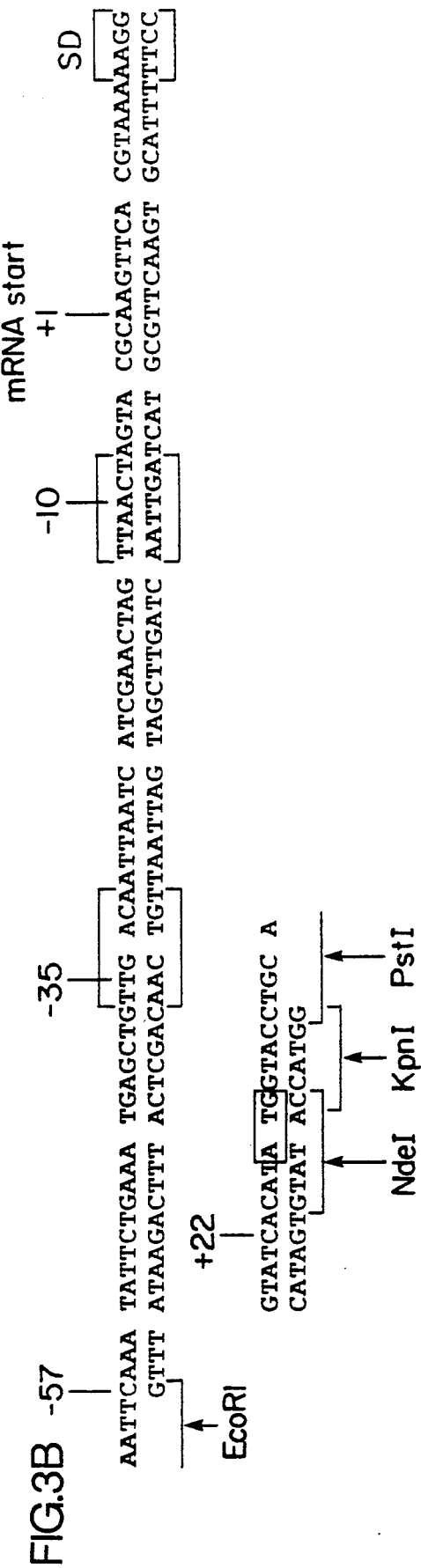

| NO. | Y POS. | AREA | MARK | % |
|---|---|---|---|---|
| 1 | 131.1 | 1065.883 | V | 0.6 |
| 2 | 133.7 | 12987.82 | V | 7.7 |
| 3 | 136.2 | 5556.37 | V | 3.3 |
| 4 | 137.9 | 7053.94 | V | 4.1 |
| 5 | 139.5 | 8592.73 | V | 5.1 |
| 6 | 140.9 | 5805.17 | V | 3.4 |
| 7 | 142.3 | 9768.41 | V | 5.8 |
| 8 | 144.2 | 14728.28 | V | 8.7 |
| 9 | 146.1 | 9365.51 | V | 5.5 |
| 10 | 147.5 | 4337.30 | V | 2.5 |
| 11 | 149.5 | 9279.39 | V | 5.5 |
| 12 | 151.4 | 7133.46 | V | 4.2 |
| 13 | 152.8 | 5452.66 | V | 3.2 |
| 14 | 154.9 | 6185.14 | V | 3.6 |
| 15 | 159.0 | 17791.73 | V | 10.5 |
| 16 | 161.1 | 4385.63 | V | 2.6 |
| 17 | 162.3 | 6006.81 | V | 3.5 |
| 18 | 164.2 | 9086.68 | V | 5.4 |
| 19 | 167.9 | 14224.00 | V | 8.4 |
| 20 | 172.8 | 1266.336 |  | 0.7 |
| 21 | 179.2 | 438.269 | V | 0.2 |
| 22 | 181.8 | 7483.05 | V | 4.4 |
| TOTAL | | 167994.6 | | |

HIGH LEVEL EXPRESSION OF BASIC FIBROBLAST GROWTH FACTOR HAVING A HOMOGENEOUS N-TERMINUS

FIELD OF THE INVENTION

This invention relates to the field of recombinant production of growth factors. In particular, the invention relates to the production of human basic fibroblast growth factor having a homogeneous N-terminus. The invention provides means and methods for high level expression and recovery of human basic fibroblast growth factor having a homogeneous N-terminus.

BACKGROUND OF THE INVENTION

Basic fibroblast growth factor (bFGF) is a protein which exhibits potent mitogenic activity on a wide variety of cell types including capillary endothelial cells. The complete amino acid sequence for bFGF derived from bovine pituitary has been determined (Esch, F., et al., *Proc Natl Acad Sci (USA)* (1985) 82:6507). Cloned DNA sequences encoding human bFGF have been isolated and the amino acid sequences determined for 131-, 146- and 154-amino acid forms of the human protein (PCT application US86/01879, published as WO 87/01728 on Mar. 26, 1987; Abraham, J. et al., *Science* (1986) 233:545; Abraham, J. et al., *The EMBO Journal* (1986) 5:2523). Analysis of the cloned DNA sequences also demonstrated that a potential initiating methionine codon lies immediately upstream of the coding sequence for the 154-amino acid form of bFGF indicating that (i) the primary translation product from this gene is 155 residues in length, and (ii) the 154-amino acid form is derived by post-translational removal of the initiating methionine. Subsequently, Florkiewicz, R. and Sommer, A. (*Proc Natl Acad Sci (USA)* (1989) 86:3978-3981) and Prats, H., et al. (*Proc Natl Acad Sci (USA)* (1989) 86:1836-1840) reported the existence of longer forms of bFGF which may be produced as the result of alternative translation initiation at leucine codons lying upstream of the methionine initiation codon for the 155-residue primary translation product.

Due in part to its potent mitogenic activity on capillary endothelial cells, bFGF promotes angiogenesis, i.e. the process of forming new capillary blood vessels. It is, therefore, quite useful as a wound healing agent in applications where it is necessary to form a new capillary bed if the wound is to heal properly.

The availability of isolated, cloned DNA sequences encoding human bFGF has made it possible, using the techniques of recombinant DNA technology, to express the protein in host cells transformed with expression vectors containing these sequences and to recover the protein for clinical use. It has been observed that expression of the 155-residue primary translation product of human bFGF and the bovine equivalent in both prokaryotic and eukaryotic hosts capable of processing off the N-terminal methionine results in the production of protein having a microheterogeneous N-terminus (see, e.g., Barr, Philip J. et al., *J Biol Chem* (1988) 263 (31):16471). We have consistently observed that expression of the 155-residue primary translation product of human bFGF in *E. coli* results in the recovery of protein having a mixed N-terminal sequence Ala-Ala-Gly-Ser-Ile-/Ala-Gly-Ser-Ile- in approximately a 70/30 ratio. Although this microheterogeneity does not appear to affect the bioactivity of the molecule, it is generally considered desirable for clinical use to obtain a homogeneous material, i.e. a protein having essentially the same N-terminal sequence from molecule to molecule.

SUMMARY OF THE INVENTION

This invention provides methods and means for high level expression of human bFGF having an essentially homogeneous N-terminus. By "essentially homogeneous" is meant that sequence analysis by the Edman degradation method indicates that the bFGF contains greater than 95%, preferably greater that 98%, material having an identical N-terminus. The invention is based on the discovery that deletion of a codon encoding one of the two alanine residues immediately following the N-terminal methionine residue of the 155-amino acid primary translation product of human bFGF results in the expression and recovery of human bFGF protein that is homogeneous at its N-terminus. Particularly, following post-translational processing of the N-terminal methionine, there is produced human bFGF of 153 amino acids in length having the uniform N-terminal sequence Ala-Gly-Ser-. Furthermore, using the *E. coli* expression vectors in Examples 3 and 5 below, it has been discovered that expression of the Ala-deletant sequence results in expression levels on the order of 50% to 100% higher than expression of the corresponding protein sequence which does not have the Ala deletion.

Accordingly, there is provided by the present invention a method for producing human bFGF having a homogeneous N-terminus which comprises expressing, in a host cell capable of post-translationally removing the N-terminal methionine, a DNA sequence encoding the amino acid sequence of the 155-amino acid form of human bFGF from which a codon for one of the two alanine residues immediately following the N-terminal methionine has been deleted; and recovering the protein. There is also provided a vector for high level expression and recovery of human basic FGF having a homogeneous N-terminus. The vector comprises a DNA sequence encoding the 155-amino acid form of human bFGF from which a codon for one of the two alanines immediately following the N-terminal methionine has been deleted, said DNA sequence being operably linked to a control sequence capable of directing its expression in a host cell. Also provided is a human bFGF composition comprising a homogeneous protein having 153 amino acids of the human bFGF sequence with the N-terminal sequence Ala-Gly-Ser-.

BRIEF DESCRIPTION OF THE DRAWINGS

FIG. 1A is a representation of an isolated native cDNA sequence encoding human bFGF and the deduced amino acid sequence of the 155-residue primary translation product. FIG. 1B is a representation of an isolated native cDNA sequence encoding bovine bFGF and the deduced amino acid sequence of the 155-residue primary translation product.

DETAILED DESCRIPTION OF THE INVENTION

Figures 1, 4:
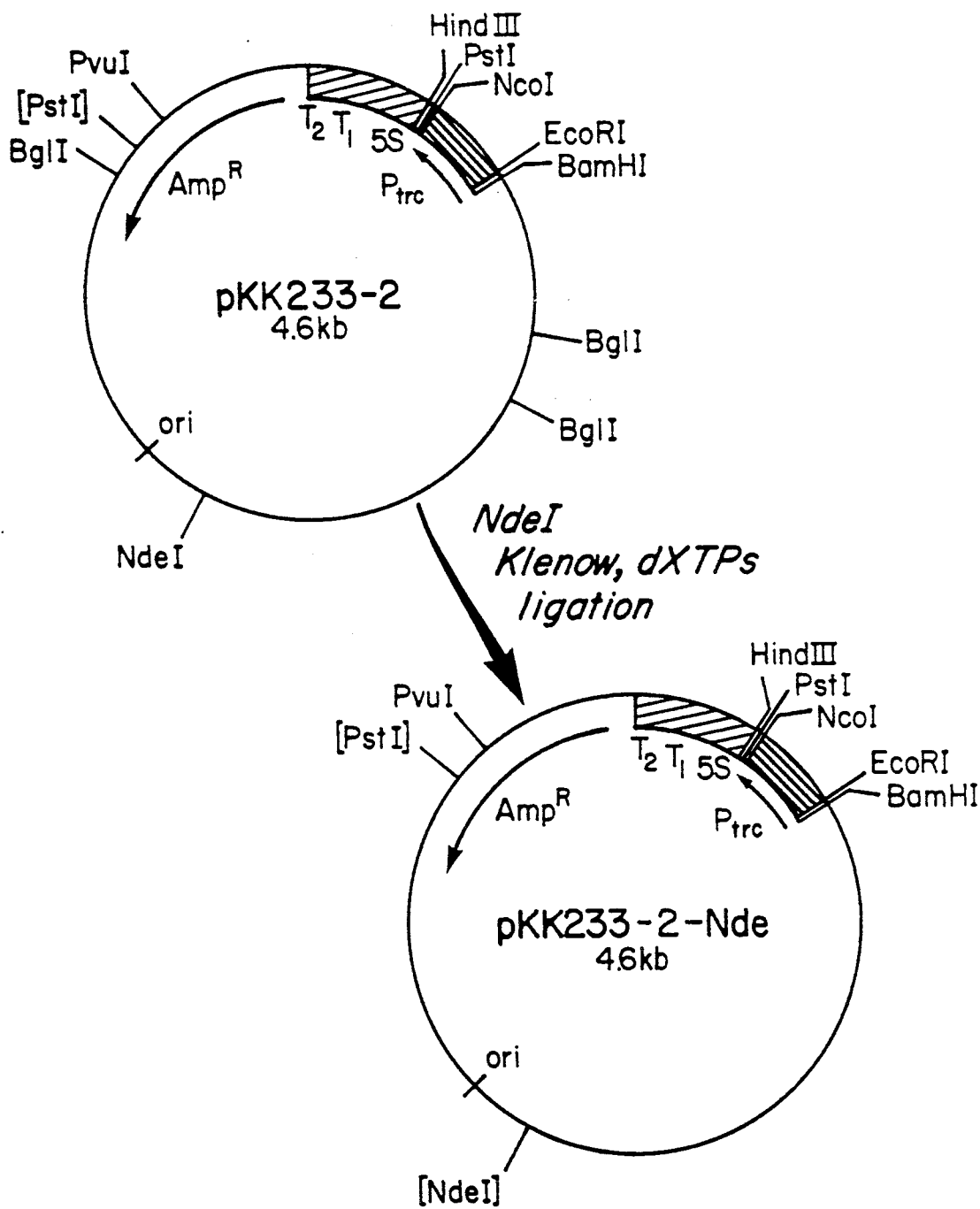
FIG. 4 illustrates the construction of pTrp-233, into which a DNA sequence encoding human bFGF was inserted to create pTsF11.

The invention employs a DNA sequence, coding for the 155-amino acid precursor form of human bFGF, from which there has been deleted a codon for one of the two alanine residues immediately following the N-terminal methionine. The encoded modified form of human bFGF is referred to hereafter as "bFGF(MAGS)" to indicate that the primary translation product has the N-terminal sequence Met-Ala-Gly-Ser-. The amino acid sequences of the 155-residue forms of human bFGF and bovine bFGF are shown in FIG. 1A and FIG. 1B, respectively. The DNA sequences shown in FIG. 1A and FIG. 1B are the native coding sequences that were determined as described in PCT publication No. WO 87/01728, the disclosure of which is incorporated herein by reference. Either of these sequences can be modified by site specific mutagenesis (Zoller, M. J., and Smith, M., $Nucleic$ $Acids$ $Res$ (1982) 10:6487 and Adelman, J. P. et al., DNA (1983) 2:183) to produce a DNA encoding an analog form of human bFGF lacking one of the alanine residues immediately after the N-terminal methionine. Due to the well-known degeneracy of the DNA code, it will be understood that other DNA sequences can be employed provided they encode the desired human bFGF sequence missing one of the N-terminal alanine residues. In a preferred embodiment, a DNA sequence is provided which encodes human bFGF missing an alanine residue, wherein a substantial portion of the DNA encoding the N-terminal portion of the molecule has been modified to reduce its G+C content by comparison with the native DNA sequence.

If desired, the entire DNA sequence encoding bFGF(MAGS) can be produced synthetically by ligating together a series of overlapping synthetic oligonucleotides which, when ligated, represent the entire desired DNA sequence. The individual oligonucleotides can be prepared by either the phosphotriester method as described by Edge, et al., $Nature$ (1981) 292:756 and Duckworth, et al., $Nucleic$ $Acids$ $Res$ (1981) 9:1691 or the phosphoramidite method as described by Beaucage, S. L. and Caruthers, M. H., $Tet$ $Letts$ (1981) 22:1859 and Matteucci, M. D. and Caruthers, M. H., $J$ $Am$ $Chem$ $Soc$ (1981) 103:3185 and can be prepared using commercially available automated oligonucleotide synthesizers. This approach has been used successfully to synthesize entire genes of considerable length.

Preferably, the DNA sequence encoding bFGF(MAGS) is produced by site specific mutagenesis of a DNA sequence encoding the full 155-amino acid precursor of human bFGF to remove one of the N-terminal alanine codons. Site specific mutagenesis can be carried out using the procedures disclosed by Zoller, M. J. and Smith, M., supra and Adelman, J. P., supra. Mutagenesis is carried out on a single-stranded DNA encoding the 155-amino acid form of human bFGF (contained in a derivative of the bacteriophage M13), using a synthetic oligonucleotide primer complementary to the single stranded DNA except for limited mismatching representing the desired mutation, i.e. deletion of one of the codons for alanine immediately following the ATG start (methionine) codon.

The size of the oligonucleotide primer is determined by the requirement for stable hybridization of the primer to the region of the gene in which the mutation is to be induced and by the limitations of the currently available methods for synthesizing oligonucleotides. The factors to be considered in designing oligonucleotides for use in oligonucleotide-directed mutagenesis (e.g., overall size, size of portions flanking the mutation site) are described by Smith, M. and Gillam, S. in $Genetic$ $Engineering:$ $Principles$ $and$ $Methods,$ Plenum Press (1981) 3:1–32. In general, the overall length of the oligonucleotide will be such as to optimize stable, unique hybridization at the mutation site with the 5' and 3' extensions from the mutation site being of sufficient size to avoid editing of the mutation by the exonuclease activity of the DNA polymerase. Oligonucleotides used for mutagenesis in accordance with the present invention usually contain from about 18 to about 45 bases, preferably from about 23 to about 27 bases. They will usually contain at least about nine bases 3' of the altered or missing codon.

The synthetic nucleotide primer omitting a codon for one of the alanine residues is hybridized to single-stranded phage such as M13, fd, or φX174 into which a strand of the DNA sequence coding for 155-amino acid bFGF has been cloned. It will be appreciated that the phage may carry either the sense strand or antisense strand of the gene. When the phage carries the antisense strand the primer is identical to the coding sequence of the region to be mutated except for a deletion of the codon that defines the alanine which is to be deleted. When the phage carries the sense strand the primer is complementary to the coding sequence of the region to be mutated except for a deletion of the triplet complementary to that which codes for the alanine residue that is to be deleted.

Conditions that may be used in the hybridization are described by Smith, M. and Gillam, S., supra. The temperature will usually range between about 0° C. and 70° C., more usually about 10° C. to 50° C. After hybridization, the primer is extended on the phage DNA by reaction with DNA polymerase I (Klenow fragment), T4 DNA polymerase, or other suitable DNA polymerase. The resulting dsDNA is converted to closed circular dsDNA with DNA ligase such as T4 ligase. DNA molecules containing single-stranded regions may be destroyed by S1 endonuclease treatment. Alternatively, the partially double-stranded preparation can be used directly without treatment with ligase or S1.

The resulting fully or partially double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after being lifted as replicas onto nitrocellulose filters or other support membranes, denatured and then hybridized with kinased synthetic primer. The wash is carried out at a temperature which permits binding of an exact match, but at which the mismatches with the original strand are sufficient to prevent binding. Plaques which hybridize with the probe are then picked, cultured, and the DNA recovered.

Also included within the scope of the present invention is the production of alanine deletants of the 155-amino acid form of human bFGF in which additional changes in amino acid sequence have been effected downstream of the N-terminal Met-Ala-Gly-Ser-. PCT publication WO89/00198, the disclosure of which is incorporated by reference, discloses a number of analogs of bFGF in which amino acid residues of the native bFGF sequence have been substituted with other amino acids in order to effect beneficial changes in the properties of the molecule. In particular, the PCT publication discloses analogs in which amino acid residues in a heparin-binding domain, at positions 128 through 138 in the 155-residue primary translation product, are substituted by neutral or negatively charged amino acid residues. Also disclosed are analogs in which one or more of the native cysteine residues, preferably those at positions 78 and 96 in the 155-residue primary translation product, are substituted by neutral amino acid residues. Any of these amino acid substitutions can be combined with the alanine deletion of the present invention. Specifically excluded from the scope of the present invention are the N-terminally shortened versions of bFGF disclosed in PCT WO 89/00198. The amino acid modifications downstream of the Met-Ala-Gly-Ser- N-terminal sequence can be effected by site specific mutagenesis of the encoding DNA as disclosed in PCT WO 89/0198, which mutation(s) can be carried out either before or after the mutation deleting the alanine codon.

Figures 2, 4:
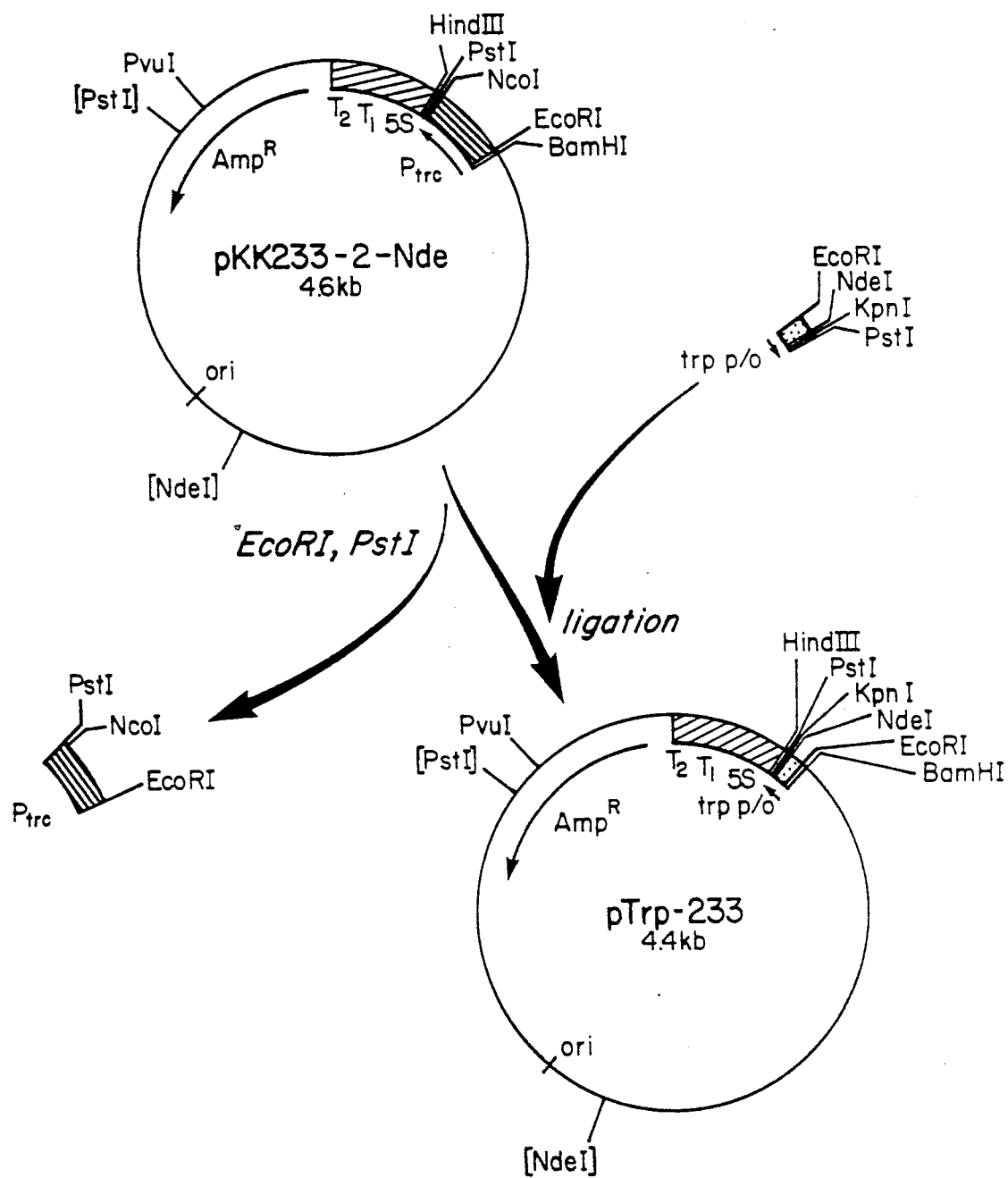
FIG. 2 is a representation of a DNA sequence encoding human bFGF. This DNA sequence was produced by replacing a portion (upstream from the indicated HhaI site) of the 5' end of the bovine sequence in FIG. 1B with a synthetic DNA sequence having reduced G+C content compared with the native bovine sequence; deleting a codon for one of the two alanine residues immediately following the N-terminal methionine; changing codons 121 and 137 in FIG. 1B to ACC and TCC, respectively, and creating a HindIII restriction endonuclease site 3' to the translation termination codon such that the cDNA sequence (i) encodes human bFGF missing one of the N-terminal alanines, and (ii) is flanked on its 5' and 3' ends with an NdeI site and a HindIII site, respectively.

Non-human mammalian bFGF corresponding to human bFGF(MAGS) can also be provided by the invention. It is known, for example, that the amino acid sequence of the 155-residue precursor of bovine bFGF differs from the human precursor protein by two amino acid residues i.e. the bovine protein has Ser rather than Thr at position 121 and Pro rather than Ser at position 137 (using a numbering system based on the 155-amino acid sequence). Thus, a DNA sequence encoding bovine protein corresponding to human bFGF(MAGS) can be prepared by mutagenesis of the DNA sequence of FIG. 2 to change the codons corresponding to amino acid residues no. 120 and 136. This can be accomplished by a single nucleotide mutation in each codon.

The DNA sequence encoding bFGF(MAGS) is inserted into an appropriate expression vector in which it is operably linked to a regulatory sequence which is capable of directing expression of the coding sequence in a host cell. "Regulatory sequence" refers to a DNA sequence or sequences which are capable, when properly ligated to the coding sequence, of effecting its expression in a host compatible with such sequences. Such regulatory sequences include at least promoters in both prokaryotic and eukaryotic hosts, and optionally, operator sequences, enhancers and transcription termination signals. Additional factors necessary or helpful in effecting expression in a particular host can be used. "Operably linked" refers to a juxtaposition wherein the components are configured so as to perform their usual function. Thus, regulatory sequences operably linked to a coding sequence are capable of effecting the expression of the coding sequence. As those skilled in the art will know, the expression vector can also have an origin of replication which is functional in the host cell to be used. Desirably, the vector also contains a phenotypic marker, such as a gene for antibiotic resistance, which allows the identification and selection of host cells carrying the vector.

The expression vector is used to transform a suitable host cell. Both prokaryotic and eukaryotic hosts can be employed. Prokaryotes most frequently are represented by various strains of *E. coli,* however, other microbial strains may be employed. *E. coli* has exhibited the ability to post-translationally process the N-terminal methionine residue of the 155-residue precursor form of human bFGF. Useful strains of *E. coli* include, for example, MC1061, DH1, RR1, C600hfl, K803, HB101, JA221, JM101, JM103 and B, with *E. coli* B being a preferred host. Plasmid vectors which contain replication sites, selectable markers and regulatory sequences derived from a species compatible with the host are used; for example, *E. coli* is typically transformed using vectors derived from pBR322, a plasmid derived by combining parts of plasmids obtained from two *Salmonella* species and an *E. coli* strain by Bolivar et al., Gene (1977) 2:95. pBR322 contains genes for ampicillin and tetracycline resistance and thus provides multiple selectable markers which can be either retained or destroyed in constructing the desired vector. Commonly used prokaryotic regulatory sequences which are defined herein to include promoters for transcription initiation, optionally with an operator, along with ribosome binding site sequences, include such commonly used promoters as the β-lactamase (penicillinase) and lactose (lac) promoter systems (Chang, et al., *Nature* (1977) 198:1056), the tryptophan (*trp*) promoter system (Goeddel, et al., *Nucleic Acids Res* (1980) 8:4057), the lambda-derived $P_L$ promoter (Shimatake, et al., *Nature* (1981) 292:128) with the N-gene ribosome binding site, and the *trp-lac* (*trc*) promoter system (Amann, E., and Brosius, J., *Gene* (1985) 40:183).

In addition to bacteria, eukaryotic cells, such as yeast or Chinese hamster ovary (CHO) cells, may also be used as hosts. Those skilled in the art will know the useful regulatory sequences, origins of replication, markers, etc. which are useful in connection with various eukaryotic hosts.

The expression vector containing the coding sequence for bFGF(MAGS) is used to transform a host cell. Depending on the host cell used, transformation is done using standard techniques appropriate to such cells. The calcium treatment employing calcium chloride, as described by Cohen, S.N., *Proc Natl Acad Sci (USA)* (1972) 69:2110 or the $RbCl_2$ method described in Maniatis, et al., *Molecular Cloning: A Laboratory Man-* ual (1982) Cold Spring harbor Press, p. 254 and Hanahan, D., *J Mol Biol* (1983) 166:557–580 may be used for prokaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al., Cell (1979) 16:777–785, may be used. Transformations into yeast may be carried out according to the method of Beggs, J.D., *Nature* (1978) 20 275:104–109 or of Hinnen, A. et al., *Proc Natl Acad Sci* (USA) (1978) 75:1929.

Transformants carrying the bFGF(MAGS) expression vector can be identified by known techniques, depending on the particular phenotypic marker used in the construction of the vector, e.g. by growth in the presence of an antibiotic such as ampicillin where an antibiotic resistance marker is employed. Various known techniques, such as restriction enzyme analysis or sequencing by the dideoxy method, can be employed to verify the correct vector construction.

Expression of bFGF(MAGS) can be effected under conditions that will depend largely on the particular vector construction and host cell used and will be readily apparent to those skilled in the art. Where the vector contains the bFGF(MAGS) DNA sequence under the control of an inducible promoter, such as the trp promoter, the transformed host cells can be used to inoculate a suitable growth medium, and grown to optimal density; expression of bFGF(MAGS) from the controlling promoter can then be induced by the addition of the appropriate inducer, e.g. 3-$\beta$-indoleacrylic acid in the case of the trp promoter. The expressed bFGF(MAGS) can be recovered by known techniques such as those employed in the art for the purification of bFGF from natural sources. In a preferred purification procedure, transformants containing the expressed protein are lysed mechanically or chemically to release the protein. After treatment with DNase and RNase, the reaction is centrifuged and the supernatant is loaded onto a heparin-Sepharose column which can be obtained commercially (Pharmacia, Inc.). After washing the column with a NaCl buffer having a salt concentration of about 1.0 M or less, the bFGF(MAGS) can be eluted from the column in 2.0 M NaCl. If desired, the heparin-Sepharose chromatography step can be repeated or combined with other known protein purification steps, such as ion exchange chromatography on S/P Sephadex or Mono S resins. For commercial scale production, copper chelate affinity chromatography may be preferable to the heparin-Sepharose chromatography, since it may be undesirable to have even a small amount of heparin in the final formulation.

Quite surprisingly, when bFGF(MAGS) was expressed in *E. coli* B, it was found that expression levels were on the order of 50% to 100% greater than expression of the corresponding wild-type (non-mutated) human bFGF using the same host-vector system and the same expression conditions. In particular, the method of the invention allows one to express bFGF(MAGS) at levels of at least 10% of the total protein expressed by the host cell. Furthermore, N-terminal amino acid analysis indicates that expression of bFGF(MAGS) in *E. coli* B results in a final protein product which has an essentially homogeneous N-terminus; that is, greater than 95%, preferably greater that 98% of the bFGF has an identical N-terminus when the protein is subjected to N-terminal sequence analysis by Edman degradation. It has been found that prokaryotic hosts such as *E. coli* are capable of processing off the N-terminal methionine residue encoded by the ATG start codon of bFGF. Accordingly, the method of the invention results in the recovery of bFGF having 153 amino acid residues with the N-terminal sequence Ala-Gly-Ser-.

The bFGF(MAGS) provided by the invention has the same utilities as the corresponding bFGF having the N-terminal sequence Ala-Ala-Gly-Ser-, or a mixed N-terminus. The bFGF(MAGS) is useful in encouraging the healing of wounds. Purified bFGF(MAGS) is generally applied topically to the traumatized tissue in order to stimulate vascularization and healing. Appropriate substrates are burns, dermal ulcers, surgical abrasions such as those of plastic surgery, or other wound situations requiring repair. Because application of bFGF(MAGS) accelerates healing, it also reduces the risk of infection.

Indications wherein bFGF(MAGS) is of value in encouraging neovascularization include musculo-skeletal conditions such as bone fractures, ligament and tendon repair, tendonitis, and bursitis; skin conditions such as burns, cuts, lacerations, bed sores, and slow-healing ulcers such as those seen in diabetes; and in tissue repair during ischemia and myocardial infarction.

Formulations of the recombinantly produced bFGF(MAGS) using available excipients and carriers are prepared according to standard methods known to those in the art. The protein can be formulated as lotions, as gels, as part of a controlled release system, or as ointments with additional active ingredients, such as antibiotics, if desired.

For topical administration, which is the most appropriate with regard to superficial lesions, standard topical formulations are employed using, for example, 0.1–100 $\mu$g of bFGF(MAGS) per $cm^2$ of affected surface area. Such solutions would be applied as seldom as just once to the affected area to as often as two times a day over a two to four week period (or possibly longer in some cases of impaired healing situations). The concentration of the bFGF(MAGS) and other ingredients in the formulation depends, of course, on the nature and severity of the wound and the nature of the subject. The dose may be lowered with time to lessen likelihood of scarring. For example, the most severe wounds, such as third degree burns, may be treated with a 100 $\mu$g/$cm^2$ dose of bFGF(MAGS), but as healing begins, the dose may be progressively dropped to approximately 0.1 $\mu$g/$cm^2$ or lower, as the wound heals. A topical formulation for FGF using BSA as carrier was disclosed by Franklin, J. D., et al., *Plastic and Reconstruc Surg* (1979) 64:766–770.

For bone and deeper (non-surface) soft tissue repair, administration is preferred locally, but by means of injection or slow release formulation implanted directly proximal to the target. Surgery may be required for such conditions as bone injuries, thus making implantation directly practical. Slow-release forms can be formulated in polymers, such as Hydron (Langer, R., et al., *Nature* (1976) 263:797–799) or Elvax 40P (Dupont) (Murray, J. B., et al., In Vitro (1983) 19:743–747). Other sustained-release systems have been suggested by Hsieh, D.S.T., et al., *J Pharm Sci* (1983) 72:17–22), and a formulation specifically for epidermal growth factor, but not preferred in the present invention, is suggested by Buckley, A., et al., *Proc Natl Acad Sci* (USA) (1985) 82:7340–7344.

As with topical administration, for sustained-release delivery, the concentration of bFGF(MAGS) in the formulation depends on a number of factors, including the nature and severity of the condition and the rate of bFGF(MAGS) release from the polymer. In general, the formulations are constructed so as to achieve a constant local concentration of about 10 times the tissue concentration, as described by Buckley, et al. (*Proc Natl Acad Sci (USA), supra*). Based on a bFGF concentration in tissue of 5–50 ng/g wet weight (comparable to EGF at 60 ng/g wet weight), release of 50–5000 ng FGF per hour is acceptable. The initial concentration, of course, depends on the severity of the wound.

It is expected that bFGF(MAGS) may act in concert, and even synergistically, with other growth factors such as epidermal growth factor (EGF), the transforming growth factors (TGF-α or TGF-β), insulin-like growth factors (IGF-1 and IGF-2), Iamin (a Gly-His-Lys tripeptide) and/or platelet-derived growth factor (PDGF). In addition, specifically for bone repair, it may act in synergy with antagonists of parathyroid hormone, since parathyroid hormone promotes bone resorption. Therefore, also included within the compositions and administration protocols of the invention are embodiments wherein the bFGF(MAGS) of the invention is administered in the same composition with, or in the same protocol with, one or more of the foregoing factors, thus more effectively to achieve the desired tissue repair.

Since bFGF(MAGS) is effective in promoting neurite outgrowth, nerve regeneration, and neuronal survival, it may be useful for treatment of certain neurological disorders such as Alzheimer's and Parkinson's diseases, amyotrophic lateral sclerosis, and general aging of the nervous system, as well as traumatic injury to the spinal cord and peripheral nerves.

Administration of the drug for these indications is preferably by implant in formulations similar to those set forth above in connection with wound healing. The drug may also be delivered by means of implants of cell cultures as in transplant therapy by treating the cultures prior to transplantation with the bFGF(MAGS) preparations of the invention or by engineering the cells by recombinant DNA technology to produce bFGF(MAGS). In addition, the bFGF(MAGS) may be injected directly to the spinal fluid, or may be applied systemically. Systemic formulations are generally as known in the art and include formulation in buffer or physiological saline, or other appropriate excipient. Dosage levels for systemic formulations are sufficient to deliver to the site of action a local concentration similar to that employed in the topical formulations described above. For tissue culture or explant maintenance, it may be supplied at 0.1–10 ng/ml of serum or culture medium.

bFGF(MAGS) is particularly useful in aiding the reformation and repair of tissues traumatized during surgery. For this use, it may be helpful to embed the bFGF(MAGS) in polymers used as surgical staples. The proteins are thus able to supplement biologically the mechanical suturing effected by the staples, and to augment and abet the "natural" healing processes in the repairing tissues.

In addition, it has been shown that angiogenic stimuli, such as those provided by the bFGF(MAGS) discussed herein, result in the release of tissue plasminogen activator (tPA) and of collagenase in vitro from endothelial cells (Gross, J L., et al., *Proc Natl Acad Sci (USA)* (1983) 80:2623). Therefore, the bFGF(MAGS) of the invention is also useful in treatment of conditions which respond to these enzymes. While it may be necessary in acute situations (such as the presence of a blood clot associated with stroke or heart attack) directly to administer large doses of tPA to dissolve the clot, for treatment of chronic propensity to form embolisms, administration of bFGF(MAGS) to maintain a suitable level of tPA in the blood stream may be desirable. Therefore, for this indication, systemic administration of the drug, using conventional means such as intramuscular or intravenous injection, is preferred.

The following examples are intended to illustrate further the practice of the invention and are not intended to limit the scope of the invention in any way. The cDNA encoding bovine bFGF used as a starting material was obtained initially by screening a bovine genomic library and obtaining a pivotal probe, followed by retrieval of additional DNA as described in detail in PCT publication WO 87/01728. However, it would not be necessary to repeat this procedure, as the sequence of the pivotal probe and of the coding regions for bovine and human bFGF are now known and could thus be constructed chemically in vitro. In addition, bacteriophage harboring human and bovine bFGF sequences are deposited at the American Type Culture Collection. Thus, the bFGF DNA sequence used as the starting material in the following examples is available from a variety of sources.

EXAMPLE 1

Construction of pTrp-233 Bacterial Expression Plasmid

A. Construction of the Synthetic Tryptophan Operon Promoter and Operator Regulatory Sequence The ten oligodeoxynucleotides shown in FIG. 3A were synthesized by the phosphotriester method and purified. 500 pmole of each oligodeoxynucleotide except 1 and 10 were phosphorylated individually in 20 μl containing 60 mM Tris-HCl, pH 8, 15 mM DTT, 10 mM MgCl$_2$, 20 μCi of [γ-$^{32}$P]-ATP and 20 units of polynucleotide kinase (P/L Biochemicals) for 30 min. at 37° C. This was followed by the addition of 10 μl containing 60 mM Tris-HCl, pH 8, 15 mM DTT, 10 mM MgCl$_2$, 1.5 mM ATP and 20 additional units of polynucleotide kinase followed by another 30 min incubation at 37° C. Following incubation the samples were incubated at 100° C. for 5 min. 500 pmole of oligodeoxynucleotides 1 and 10 were diluted to 30 μl in the above buffer without ATP.

16.7 pmole of each oligodeoxynucleotide constituting a double stranded pair (e.g. oligodeoxynucleotides 1 and 2, 3 and 4, etc. FIG. 3A) were mixed and incubated at 90° C. for 2 min followed by slow cooling to room temperature. Each pair was then combined with the others in the construction and extracted with phenol/chloroform followed by ethanol precipitation. The oligodeoxynucleotide pairs were reconstituted in 30 μl containing 5 mM Tris-HCl, pH 8, 10 mM MgCl$_2$, 20 mM DTT, heated to 50° C. for 10 min and allowed to cool to room temperature followed by the addition of ATP to a final concentration of 0.5 mM. 800 units of T4 DNA ligase were added and the mixture incubated at 12.5° C. for 12–16 hours.

The ligation mixture was extracted with phenol/chloroform and the DNA ethanol precipitated. The dried DNA was reconstituted in 30 μl and digested with EcoRI and PstI for 1 hour at 37° C. The mixture was extracted with phenol/chloroform and ethanol precipitated followed by separation of the various double stranded DNA segments by electrophoresis on an 8% polyacrylamide gel, according to the method of Laemmli, *Nature* (1970) 227:680. The DNA fragments were visualized by wet gel autoradiography and a band corresponding to approximately 100 bp in length was cut out and eluted overnight. The excised synthetic DNA fragment was ligated to plasmids M13mp8 or M13mp9 (Messing, J. and Vieira, J., *Gene* (1982) 19:269) similarly digested with EcoRI and PstI, and submitted to dideoxynucleotide sequence analysis (Sanger, F., et al., *Proc Natl Acad Sci* (USA) (1977) 74:5463) to confirm the designed sequence as shown in FIG. 3A. The M13 derivative containing the correct sequence was named M13-trp. The designed sequence in M13-trp contains the promoter (−35 and −10 regions) and operator regions of the tryptophan (trp) operon as well as the ribosome binding region of the trp operon leader peptide (FIG. 3B). Analogous sequences to that shown in FIG. 3B have been proven to be useful in the expression of heterologous proteins in E. coli (Hallewell, R. A., and Emtage, S., *Gene* (1980) 9:27, Ikehara, M., et al., *Proc Natl Acad Sci (USA)* (1984) 81:5956).

B Construction of the Synthetic trp Promoter/Operator-Containing Plasmid, pTrp-233

Plasmid pKK233-2 (FIG. 4A; Amann, E. and Brosius, J., supra) was digested to completion with NdeI followed by the filling in of the termini by the method of Maniatis, et al., *Molecular Cloning*, Cold Spring Harbor Laboratories (1982) at p. 394, with 5 units of E. coli DNA Polymerase I, Klenow fragment (Boehringer-Mannheim, Inc.) and the addition of dATP, dCTP, dGTP and TTP to 50 µM. This was incubated at 25° C. for 20 min. Following phenol/chloroform extraction and ethanol precipitation, the NdeI-digested DNA was re-ligated and transformed into E. coli (Nakamura, K., et al., *J Mol Appl Genet* (1982) 1:289) The resulting plasmid lacking the NdeI site was designated pKK233-2-Nde (FIG. 4B).

Twenty nanograms of plasmid pKK233-2-Nde was digested to completion with EcoRI and PstI followed by calf intestinal phosphatase treatment (Boehringer-Mannheim) in accordance with Maniatis, et al., supra at pp. 133–134. Fifty nanograms of the synthetic trp promoter/operator sequence were obtained from M13-trp (described above) by digesting the replicative form (double-stranded DNA form) of this phage with EcoRI and PstI, and were mixed with ten nanograms of EcoRI-PstI digested pKK233-2-Nde. After ligation with T4 DNA ligase as described, the mixture was transformed into E. coli JA221 lpp−/I'lacI. Transformants were screened for the presence of plasmid DNA containing the 100 bp EcoRI-PstI synthetic trp promoter/operator; the correct plasmid was then isolated and designated pTrp-233. A plasmid map of the 4.4-kb plasmid pTrp-233 is shown in FIG. 4C.

EXAMPLE 2

Construction of Plasmid pTsF11

A. Construction of a cDNA Sequence Encoding Human Basic Fibroblast Growth Factor The bovine basic FGF cDNA contained in the clone λBB2 was used to develop hybridization probes to isolate basic FGF clones from human cDNA and genomic libraries as described in PCT publication WO 87/01728; Abraham, J. A. et al , *Science* (1986), supra; and Abraham, J. A. et al., *The EMBO Journal* (1986), supra, all of which are incorporated herein by reference.

There are two amino acid differences between the 155-residue precursor forms of bovine basic FGF and human basic FGF: at position 121, where the bovine protein has Ser and the human protein has Thr; and at position 137, where the bovine protein has Pro and the human has Ser. These differences correspond to a single nucleotide difference, in each case, in the codon for the amino acid at that position; therefore, a bovine cDNA may conveniently be modified by site-specific mutagenesis as described below to encode the human protein, and, indeed, standard site-specific mutagenesis techniques were used to alter these codons. The λBB2 clone (ATCC No. 40196) was digested with EcoRI and the 1.4 kb region spanning the bFGF protein-encoding sequence was ligated into the EcoRI site of M13mp8, and phage carrying the insert in the correct orientation were recovered. A first round of in vitro mutagenesis was carried out in the presence of three oligonucleotides: the "universal" primer, a 17-mer; the mutagenic 16-mer 5'-GAAATACACCAGTTGG-3', which alters the coding sequence at codon 121, and the mutagenic 17-mer 5'-ACTTGGATCCAAAACAG-3', which alters the sequence at codon 137. The resulting mutagenized phage was then subjected to a second round of in vitro primer-directed mutagenesis to create a HindIII site 34 bp downstream from the translation termination codon using the mutagenic 25-mer, 5'-TTTTACATGAAGCTTTATATTTCAG-3'. The resultant mutated DNA was sequenced by dideoxynucleotide sequence analysis (Sanger et al., supra) to confirm that the desired mutagenesis had occurred. The approximately 640 bp fragment spanning the FGF coding region was excised with HindIII from the replicative form of the mutated M13 phage DNA and ligated into HindIII-digested pUC13 (Messing, J., *Methods Enzymol* (1983) 101:20) to obtain the intermediate plasmid pJJ15-1.

B Construction of Human bFGF cDNA with Synthetic Coding Region for N-terminal End In order to lower the G+C content of the 5' end (the first 125 bp) of the coding region contained in pJJ15-1, a synthetic DNA fragment was constructed with the sequence shown below using the synthetic oligonucleotides listed above the contiguous sequence. The oligonucleotides were annealed in pairs, ligated together sequentially, and ligated into HindIII-cut M13mp9. The sequence of the synthetic 135 bp insert cloned into M13mp9 was confirmed by dideoxy sequencing. The replicative form of the M13mp9 phage carrying the synthetic fragment was digested with HindIII and the 135 bp fragment was isolated. This fragment was ligated into HindIII-cut pUC9. The resulting plasmid was then digested with NdeI and HhaI and the 126 bp subfragment of the synthetic insert was isolated. This 126 bp NdeI to HhaI subfragment was joined to the 377 bp HhaI-to-HindIII DNA fragment from JJ15-1 that spans approximately the carboxy-terminal three quarters of the basic FGF coding sequence, and was then ligated into the NdeI and HindIII sites of the expression vector pTrp-233 to yield the plasmid pTsF11 (FIG. 5A, 5B).

Construction of Synthetic Coding Region for the Amino Terminal Region of bFGF:

| Number | Sequence |
|---|---|
| 1670 | 5'-pAGCTTCATATGGCTGCTGGTTCTATCACTACC |
| 1623R | 5'-pCTGCCAGCTCTGCCAGAAGACGGTGGTT |
| 1624R | 5'-pCTGGTGCCTTCCCACCAGGTCACTTCAA |
| 1625R | 5'-pAGACCCAAAACGTCTGTACTGCAAAAAC |
| 1680 | 5'-pGGTGGTTTCTTCCTGCGCA |
| 1679 | 5'-pTAGAACCAGCAGCCATATGA |
| 1622 | 5'-pTCTTCTGGCAGAGCTGGCAGGGTAGTGA |
| 1619 | 5'-pACCTGGTGGGAAGGCACCAGAACCACCG |
| 1626 | 5'-pAGTACAGACGTTTTGGGTCTTTGAAGTG |
| 1673 | 5'-pAGCTTGCGCAGGAAGAAACCACCGTTTTTGC |

```
         HindIII       NdeI
            11          21          31          41          51
         AGCTTCATATG GCTGCTGGTT CTATCACTAC CCTGCCAGCT CTGCCAGAAG
              AGTATAC CGACGACCAA GATAGTGATG GGACGGTCGA GACGGTCTTC 61          71          81          91         101
         ACGGTGGTTC TGGTGCCTTC CCACCAGGTC ACTTCAAAGA CCCAAAACGT
         TGCCACCAAG ACCACGGAAG GGTGGTCCAG TGAAGTTTCT GGGTTTTGCA HhaI
           111         121         131
         CTGTACTGCA AAAACGGTGG TTTCTTCCTG CGCA
         GACATGACGT TTTTGCCACC AAAGAAGGAC GCATTCGA
                                          HindIII
```

EXAMPLE 3

Production of pTsF-9ΔβgaI Expression Vector for bFGF

Figures 1, 5:
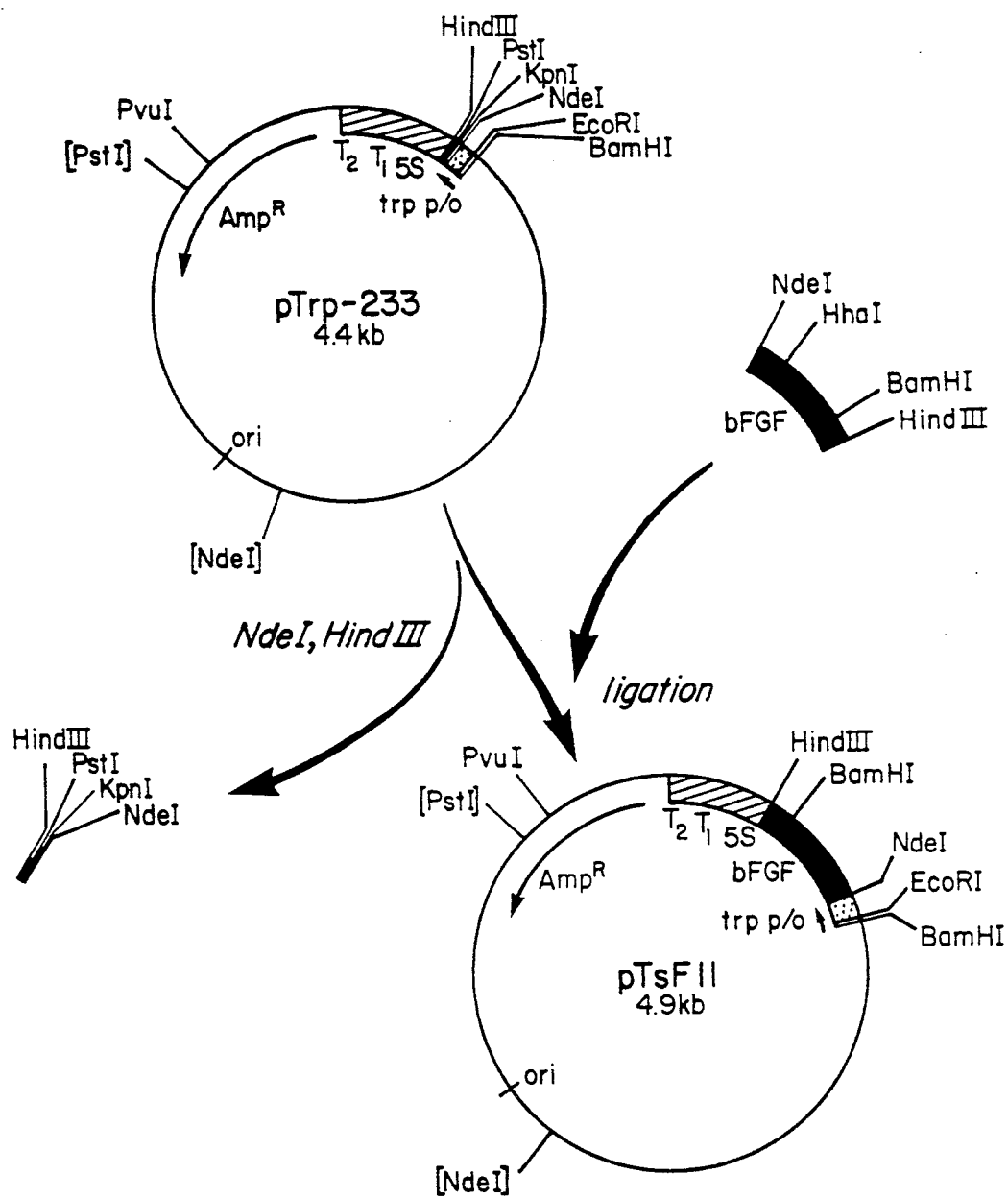
FIG. 5 is a schematic illustration of the preparation of pTsF-9Δβgal, an expression vector for human bFGF.
Figures 2, 5:
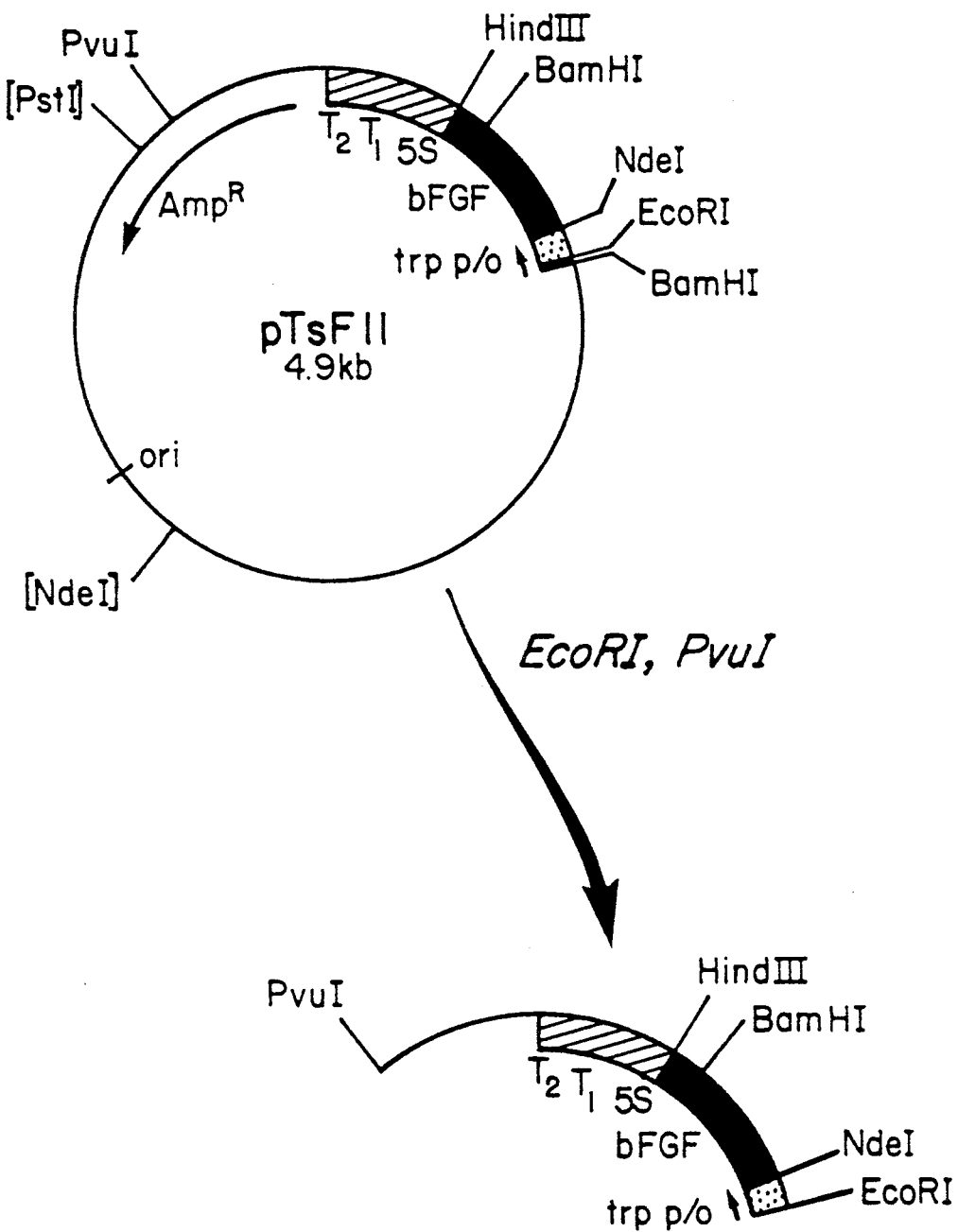
Figures 3, 5:
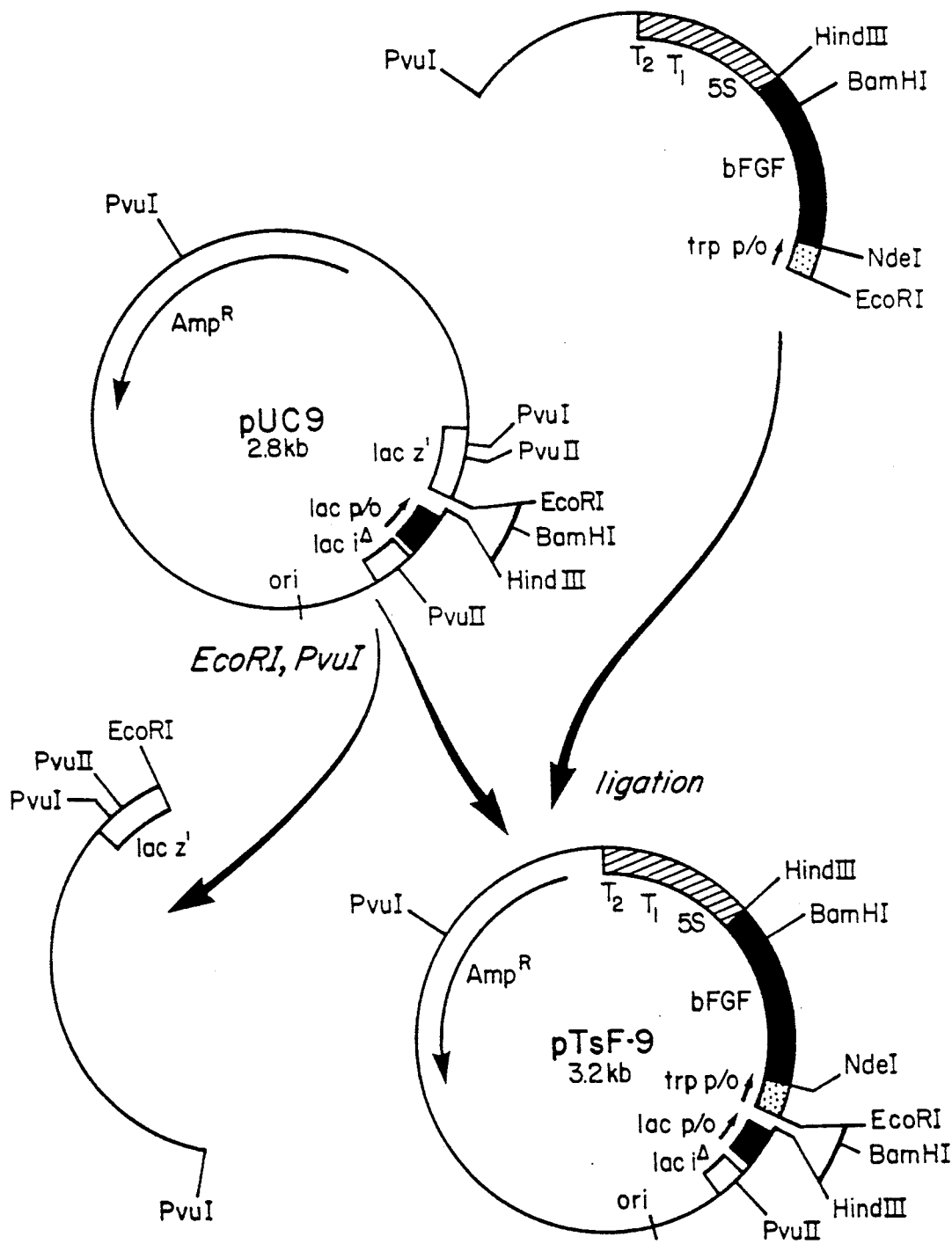
FIG. 3 illustrates a series of synthetic oligodeoxynucleotides (A) that were ligated to form a trp promoter/operator sequence (B) used to control expression of the DNA sequences of the invention.
Figures 4, 5:
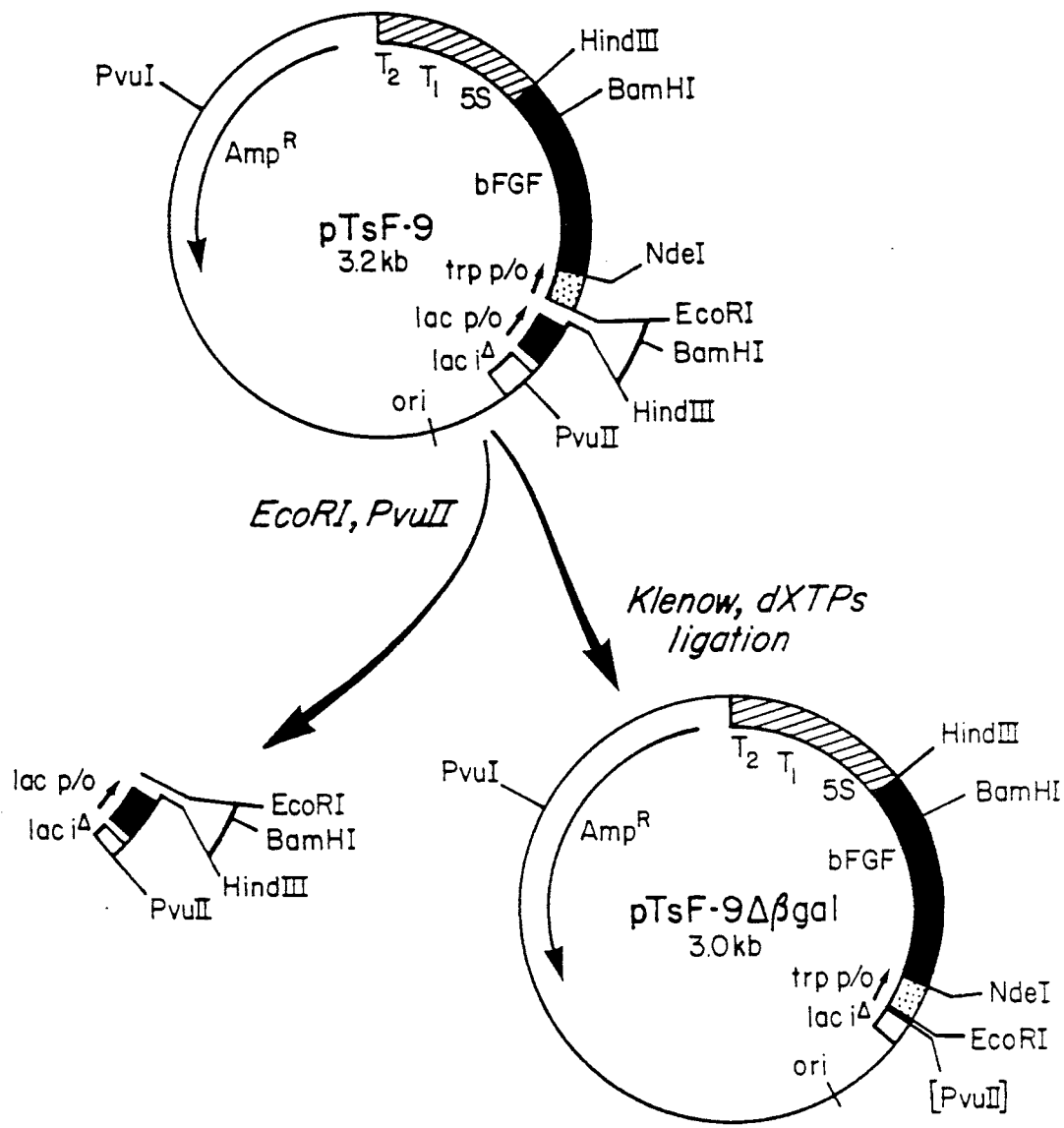

A high-copy number expression vector for expressing bFGF under the control of the trp promoter/operator was prepared according to the following procedure, which is illustrated in FIG. 5. The plasmid pUC9 (FIG. 5D; Vieira, J and Messing, J., Gene (1982) 19:259), containing an origin of replication (ori) functional in E. coli, an ampicillin resistance gene, a lac promoter/operator and a polylinker region, was digested with PvuI (New England Biolabs) and EcoRI (New England Biolabs) for 3.25 hours according to the manufacturer's instructions.

Concurrently, pTsFll DNA (FIG. 5B) was incubated as above with PvuI and EcoRI. The pUC9 and pTsF11 fragments generated by digestion with the two restriction enzymes were ligated in the presence of T4 DNA ligase. The ligation reaction was transformed into E. coli B. Plasmid DNA from ampicillin resistant colonies of transformants was analyzed by plasmid size and restriction analysis to isolate a plasmid in which the appropriate fragment of pTsF11 (the ~1.5 kb PvuI-EcoRI fragment containing the trp promoter/operator region, the bFGF coding region, the transcription termination sequences and the 5' half of the Amp gene) was ligated to the ~1.7 kb PvuI-EcoRI fragment of pUC9 (containing the origin of replication and 3' half of the Amp gene) in the orientation shown in FIG. 5E. This plasmid was designated pTsF-9.

pTsF-9 DNA was incubated with PvuII and EcoRI according to the manufacturer's directions. The overhangs at the EcoRI cleavage sites were filled in by incubating the DNA with deoxynucleoside triphosphates and the Klenow fragment of DNA Polymerase I. The DNA was recircularized by blunt end ligation in the presence of T4 DNA ligase. The ligation reaction was used to transform E. coli B to ampicillin resistance. Plasmid DNA from single colony transformants was analyzed by plasmid size and restriction analysis to isolate the plasmid identified as pTsF-9Δβgal in FIG. 5F. Blunt end ligation of the filled-in EcoRI site and the PvuII site results in restoration of the EcoRI site in pTsF-9Δβgal. The plasmid pTsF-9Δβgal contains the bFGF coding sequence under the control of the trp promoter/operator, as well as an ampicillin resistance gene and an origin of replication functional in E. coli.

EXAMPLE 4

Production of DNA Sequence Encoding bFGF(MAGS)

Plasmid FGFt7910 was constructed by ligating the ~590 bp EcoRI-HindIII DNA fragment of pTsF11 (comprising the trp promoter/operator region and the DNA encoding the 155-residue precursor form of human bFGF) into the EcoRI-HindIII sites of M13mp9. Once the single-stranded DNA of FGFt7910 was isolated, in vitro mutagenesis was carried out, as described by Zoller and Smith, supra, using a synthetic oligonucleotide coding for a portion of the N-terminus of bFGF that was missing a codon for one of the two alanines immediately following the methionine encoded by the ATG start codon. This mutagenesis resulted in the deletion of one of the codons for alanine as shown below:

ATG GCT GCT GGT TCT ATC...

Met Ala Ala Gly Ser Ile ...

⟶

ATG GCT GGT TCT ATC...

Met ALA Gly Ser Ile ...

One μg of the single stranded DNA was hybridized with 5 ng of the phosphorylated mutagenic oligonucleotide 5'-pGTATCACATATGGCTGGTTCTATC-3' and 1 ng of the M13 universal sequencing primer (17 mer purchased from P.L. Biochemicals) for 5 to 15 minutes at 55° C. in 0.01 ml solution of 10 mM Tris-HCl pH 7.5, and 10 mM MgCl₂. The reaction was cooled to room temperature and then added to 0.01 ml of 0.12 mM of each of the deoxynucleoside triphosphates dATP, dGTP, dCTP and TTP, 5 units Klenow fragment of DNA Polymerase I (Boehringer Mannheim), 20 units of T4 DNA ligase (New England Biolabs), and incubated for 4-6 hours at 15° C. An aliquot (0.002 ml) of the reaction was then added to competent E. coli JM101 bacteria and plated overnight on L agar plates at 37° C. The DNA of the resulting M13 plaques was transferred to each of two nitrocellulose filters, baked under vacuum at 80° C. for 2 hours and then incubated for 2 hours at 42° C. in prehybridization solution: 6×SSC (1×SSC is 150 mM NaCl, 15 mM sodium citrate, pH 7.0), 0.1% sodium dodecyl sulfate (SDS), 2×Denhardt's (0.04% ficoll, 0.04% polyvinylpyrrolidone, 0.04% bovine serum albumin) and 0.4 mg/ml of denatured salmon sperm DNA. The filters were then incubated for 3 hours at 42° C. with fresh pre-hybridization solution containing the mutagenic oligonucleotide which had been 5'-end labeled with [$\gamma$-$^{32}$P]-ATP and T4 polynucleotide kinase. The filters were then washed with 4×SSC at room temperature for 15 minutes, once for 15 minutes at 65° C., once at room temperature in TMACl solution (3M tetramethylammonium chloride, 50 mM Tris-HCl, pH 8.0, 2 mM EDTA, 0.1% SDS) and once at 65° C. in TMACl solution, and then used to expose X-ray film overnight at room temperature. Clones corresponding to dark duplicating positives on the X-ray film were then picked from the original plate, the DNA was isolated and then analyzed for the mutated sequence by dideoxy sequencing. The replicative form DNA of the mutated M13 clone was prepared, digested with EcoRI and HindIII, and the DNA fragment encoding the mutated basic FGF was isolated by agarose gel electrophoresis. The sequence of the bFGF coding region in this fragment is given in FIG. 2.

EXAMPLE 5

Construction of Expression Vector for bFGF(MAGS)

Figures 1, 6:
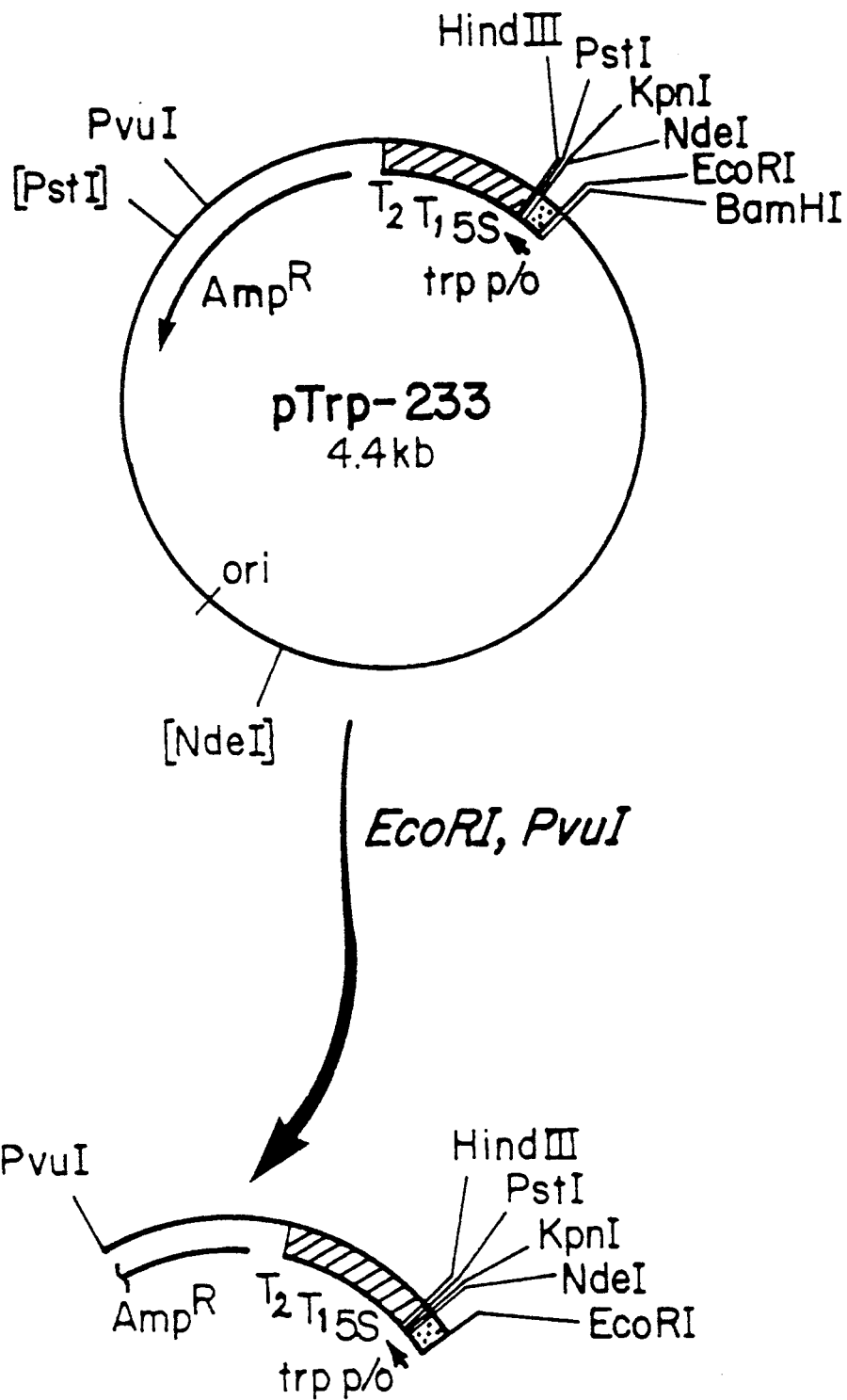
FIG. 6 is a schematic illustration of the preparation of pTsF-9Δβgal-GM-2, an expression vector suitable for insertion of the bFGF(MAGS) coding sequence.
Figures 2, 6:
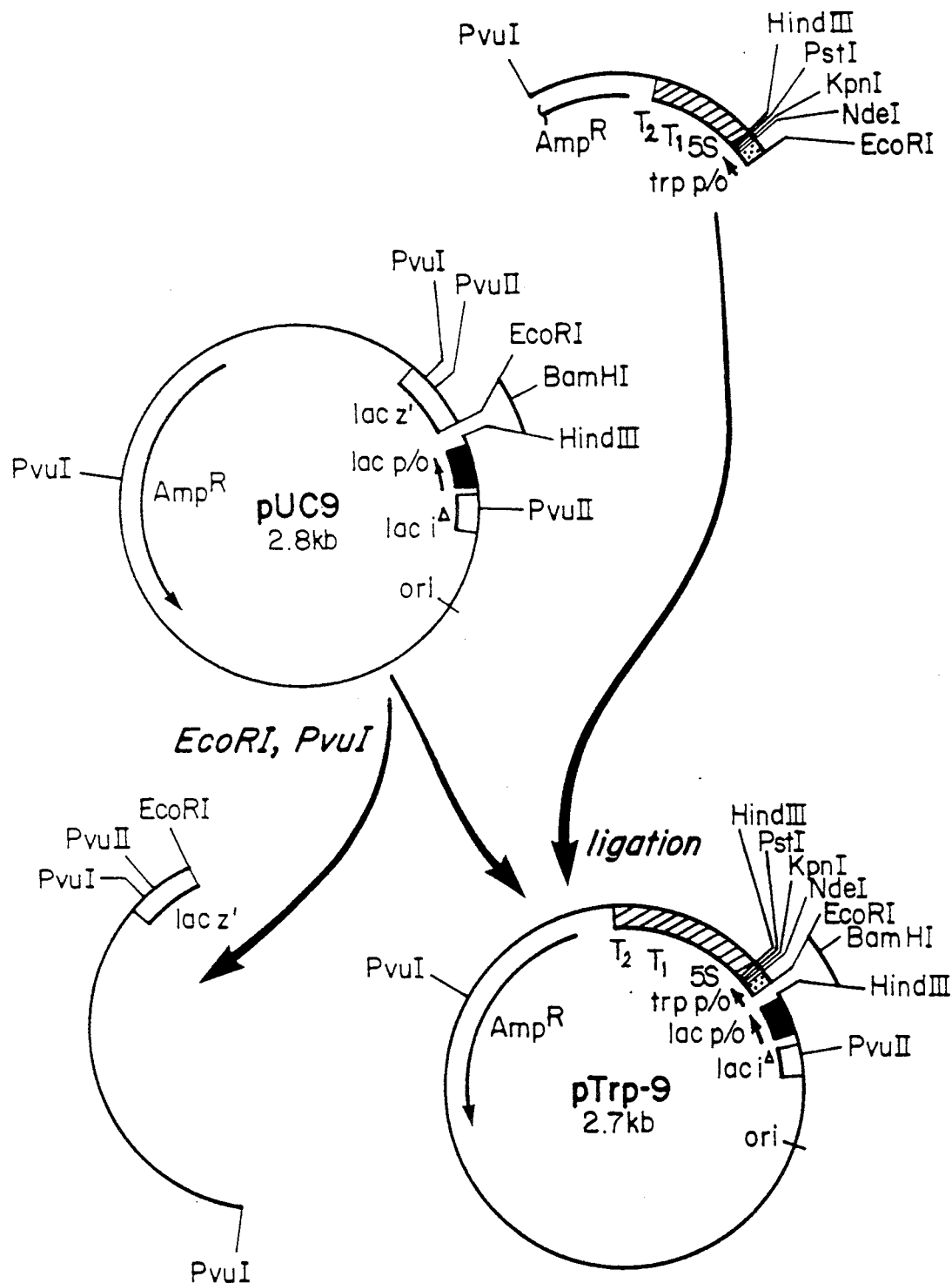
Figures 3, 6:
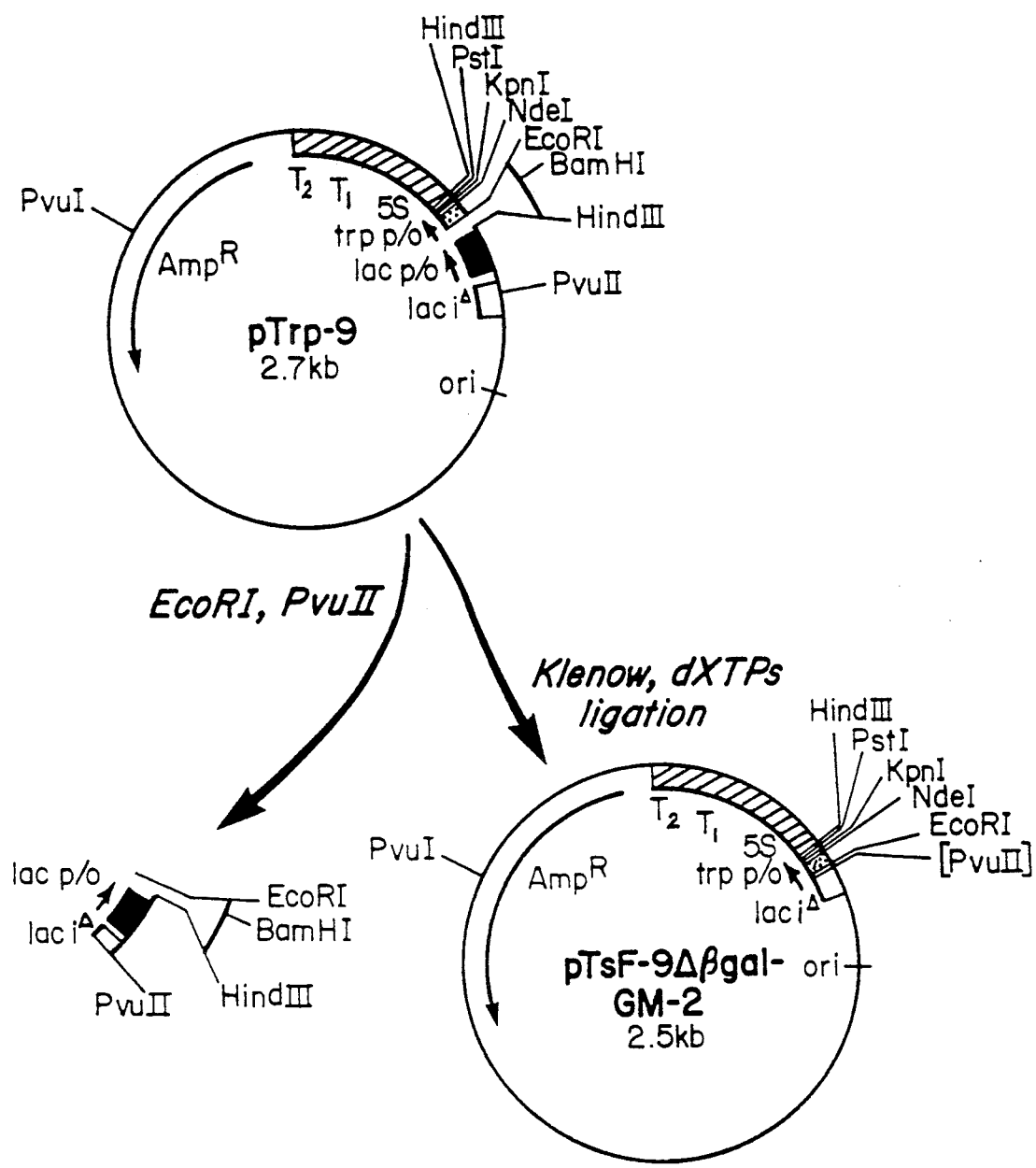

An expression vector suitable for insertion of the DNA fragment encoding bFGF(MAGS) was prepared according to the procedure illustrated in FIG. 6. The previously described plasmid pTrp-233 (FIG. 5A, FIG. 6A) was digested with EcoRI and PvuI according to the manufacturer's instructions and the fragment containing the trp promoter/operator was isolated. Concurrently, pUC9 was digested with EcoRI and PvuI and the fragment containing the origin of replication was isolated. The isolated fragments were ligated in the presence of T4 DNA ligase to produce pTrp-9, a plasmid containing the trp promoter/operator and polylinker region from pTrp-233 and the origin of replication, lac promoter/operator and polylinker from pUC9 (FIG. 6C). pTrp-9 was digested with EcoRI and PvuII and the EcoRI ends were filled in using DNA Polymerase I, Klenow fragment and deoxynucleoside triphosphates, as described above. The DNA was recircularized by blunt end ligation in the presence of T4 DNA ligase. The ligation reaction was used to transform E. coli B to ampicillin resistance. Plasmid DNA from single colony transformants was analyzed by plasmid size and restriction analysis to isolate the plasmid identified as pTsF-9$\Delta\beta$gal-GM-2 (FIG. 6D).

Plasmid pTsF-9$\Delta\beta$gal-GM-2 was incubated with EcoRI and HindIII in accordance with the manufacturer's directions and the large fragment, containing the ampicillin resistance gene and origin of replication, was isolated on an agarose gel. The EcoRI-HindIII fragment containing the bFGF(MAGS) coding sequence and trp promoter/operator (Example 4) was then ligated to the isolated fragment of pTsF-9$\Delta\beta$gal-GM-2 in the presence of T4 DNA ligase. The ligation was used to tranform competent E. coli W3110 cells, which were then grown overnight on L agar plates supplemented with 100 $\mu$g/ml ampicillin. Colonies were selected and grown in L broth supplemented with 100 $\mu$g/ml ampicillin, and plasmid DNA was then isolated from the bacteria and analyzed by restriction digestion analysis to confirm the desired structure. The resultant plasmid, designated pTsF-9$\Delta\beta$gal(MAGS), is identical to pTsF-9$\Delta\beta$gal except for the substitution of the bFGF(MAGS) coding sequence for the bFGF coding sequence.

EXAMPLE 6

Expression of bFGF and bFGF(MAGS)

Figure 7:
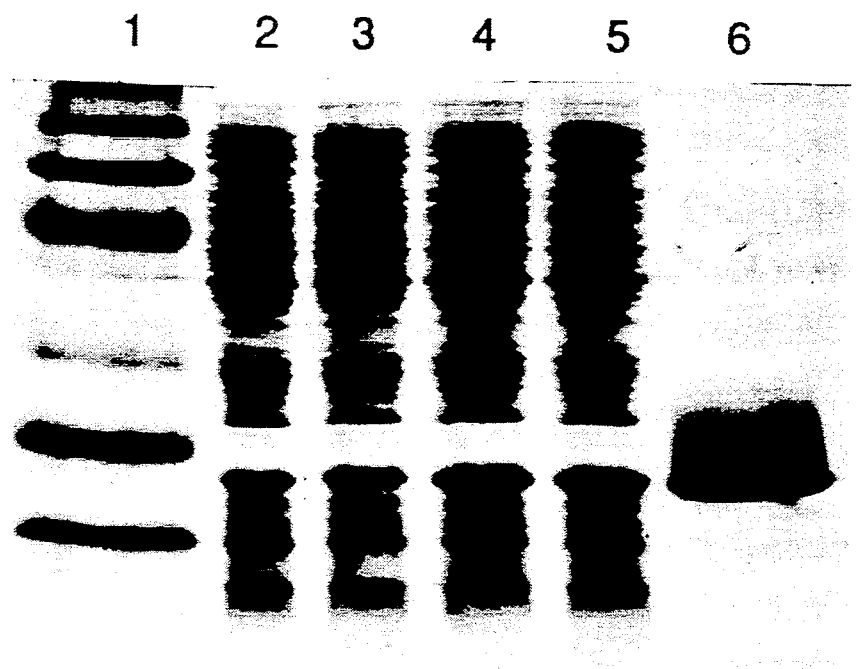
FIG. 7 is a photograph of a Coomassie blue stained SDS-PAGE gel on which the expression products of $E.$ $coli$ transformed with DNA sequences encoding human bFGF were electrophoresed alongside the expression products of $E.$ $coli$ transformed with DNA sequences of the invention encoding the alanine deletant form of human bFGF.
Figure 8A:
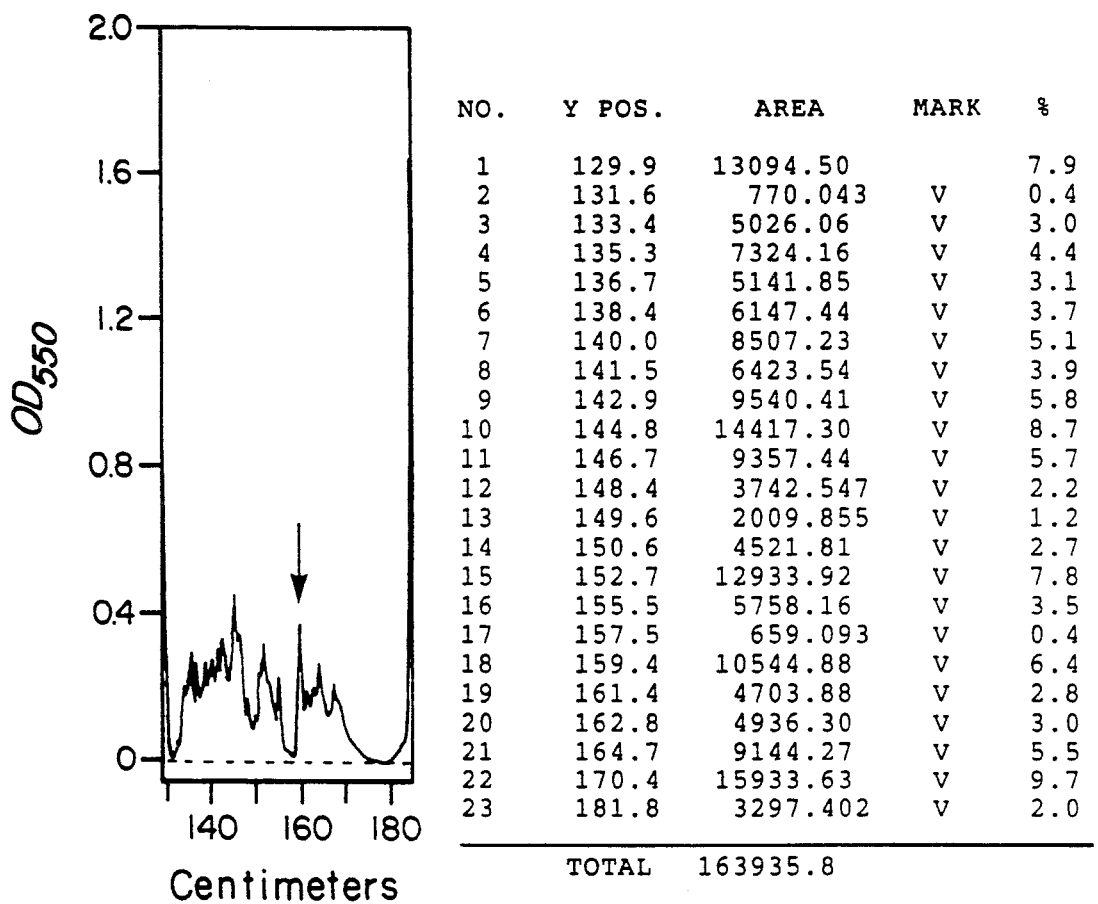
FIGS. 8A, 8B, 8C and 8D are a series of scanning densitometry plots of the protein in lanes 2 through 5, repectively of the SDS-PAGE gel of FIG. 7.
Figure 8B:
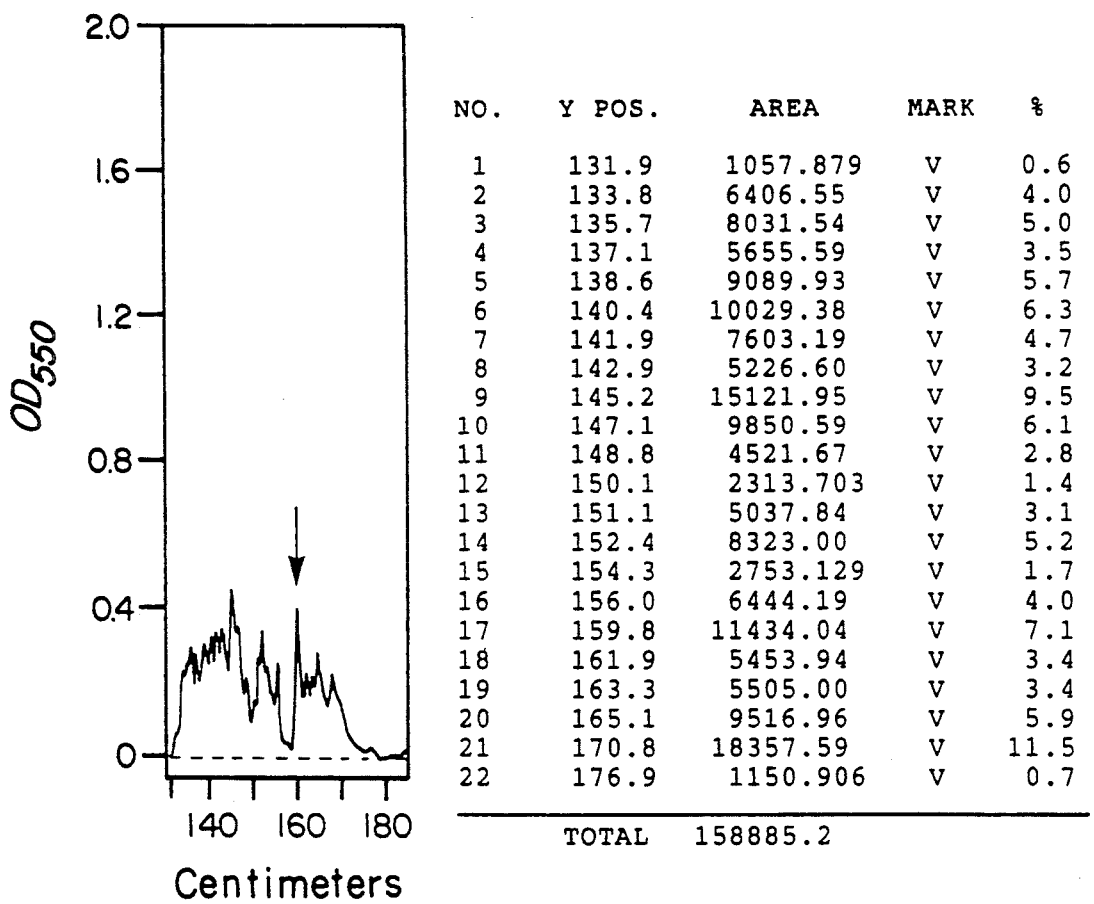
Figure 8C:
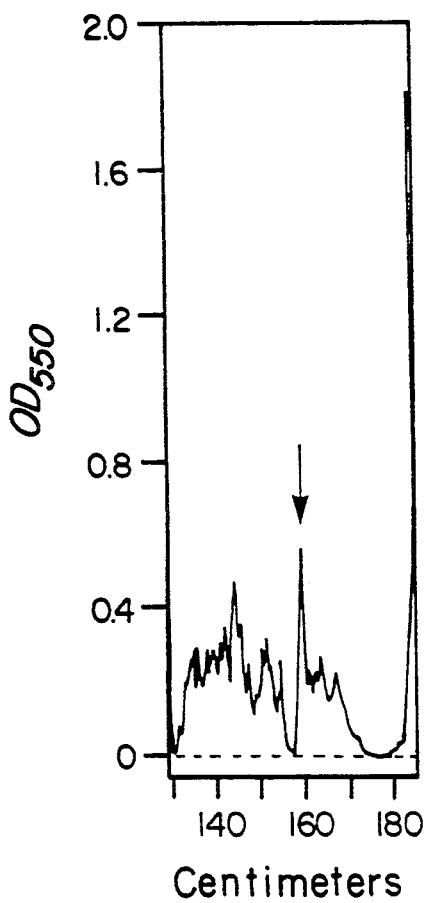
Figure 8D:
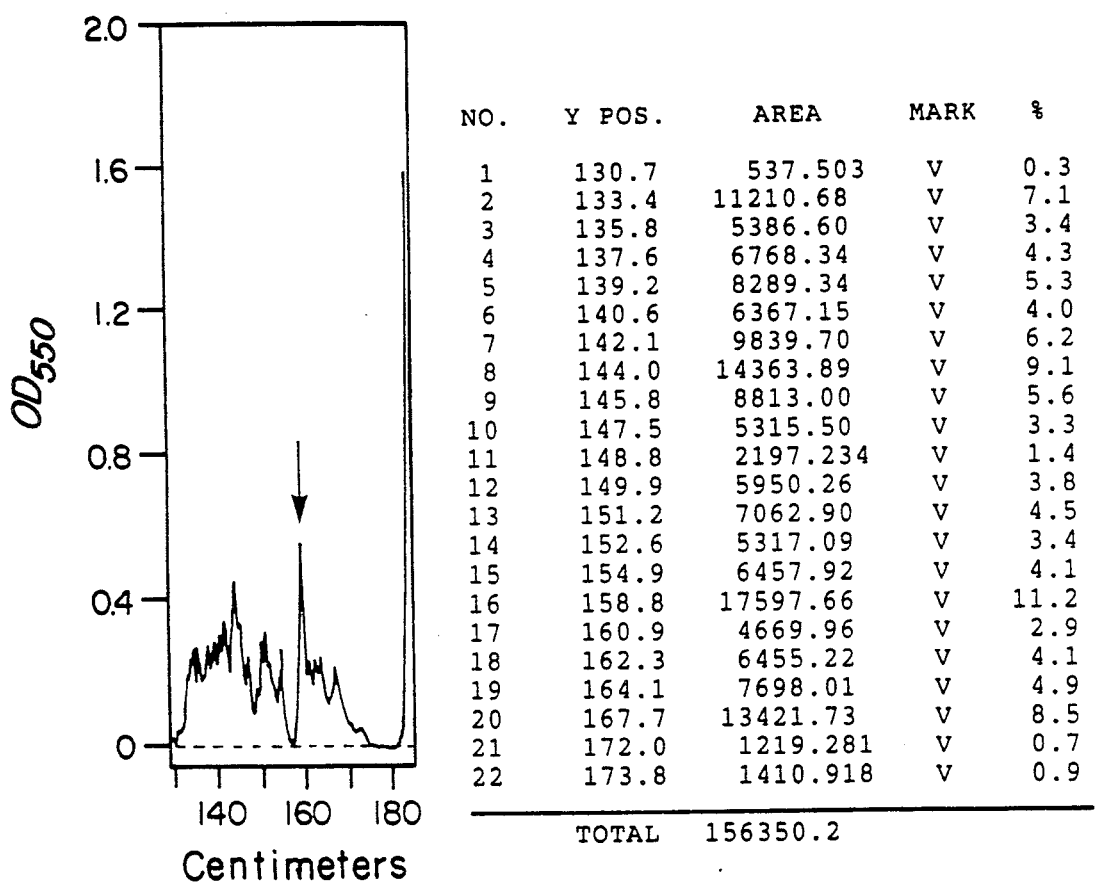

The plasmids pTsF-9$\Delta\beta$gal and pTsF-9$\Delta\beta$gal(MAGS) were separately transformed into E. coli B cells. Single colonies were used to inoculate cultures in L+amp medium, which were then grown for 5 hours at 30° C. These cultures were used in turn to seed expression cultures (1 to 100 dilution into M9 salts containing 0.5% casamino acids, 0.4% glucose, 2 $\mu$g/ml thiamine, 0.1 mM CaCl$_2$, 0.8 mM MgSO$_4$, and 50 $\mu$g/ml ampicillin). The trp promoter was induced with the addition of 50 $\mu$g/ml 3-$\beta$-indoleacrylic acid, and the cultures were grown overnight at 30° C. After 14 to 18 hours the A$_{550}$ was determined and one absorbance unit of cell pellet was resuspended in 100 $\mu$l of SDS-containing polyacrylamide gel loading buffer and boiled. 10 $\mu$l of the resulting supernatant was loaded onto a 15% acrylamide-SDS gel and electrophoresed. The gel was stained with Coomassie blue. FIG. 7 is a photograph of a stained gel with molecular weight markers in lane 1. Lanes 2 and 3 were loaded with protein extracted from two cultures of pTsF-9$\Delta\beta$gal transformants. Lanes 4 and 5 were loaded with protein extracted from two cultures of pTsF-9$\Delta\beta$gal(MAGS) transformants. Lane 6 contains a bFGF standard. The bands corresponding to bFGF(MAGS) in lanes 4 and 5 are visibly darker than the bands corresponding to bFGF in lanes 2 and 3.

The relative concentrations of the various protein species in lanes 2 through 5 were determined by scanning densitometry. FIGS. 8A-8D show the densitometry plots for each of the lanes 2-5 respectively. The peaks representing bFGF or bFGF(MAGS) are labeled by arrows. The amount of bFGF or bFGF(MAGS) expressed relative to the total cell protein was calculated for each of the cultures, based on the area under the curve in the densitometer plot. The average expression level for the two cultures transformed with pTsF-9$\Delta\beta$gal (FIGS. 8A-8B) was 6.7% of total cell protein, whereas the average expression level for the two cultures transformed with pTsF-9$\Delta\beta$gal(MAGS) (FIGS. 8C-8D) was 10.8% of total cell protein.

EXAMPLE 7

Determination of N-Terminal Sequence of bFGF(MAGS)

Using a procedure similar to that of Example 6, E. coli B cells transformed with pTsF-9$\Delta\beta$gal(MAGS) were grown in two liters of M9 media containing casamino acids and 50 $\mu$g/ml ampicillin. The culture was grown to an optical density of 0.58 (monitored at 550 nm) and induced g/ml 3-μ-indoleacrylic acid, after which it was incubated with shaking overnight at 30° C. The culture was centrifuged and the cell pellet was resuspended in 30 ml of mM Tris-HCl pH 7.5, 5 mM EDTA, 1 mM phenylmethylsulfonyl fluoride and 0.5 mg/ml lysozyme. After 30 minutes on ice, the suspension was sonicated to rupture the cells. 100 μg each of RNase and DNase were added. After 30 minutes on ice, the mixture was centrifuged and the supernatant was saved for purification.

The supernatant was applied to a column of SP-Sephadex (2.5 cm×2 cm) equilibrated with 20 mM sodium phosphate pH 7, 5 mM EDTA. The column was washed with the same buffer until the absorbance at 280 nm returned to baseline levels. The protein was eluted from the column with 20 mM sodium phosphate pH 7, 5 mM EDTA, 500 mM NaCl.

The 500 mM NaCl bump from the SP-Sephadex column was loaded onto a column of heparin-Sepharose (2.5 cm×2 cm) equilibrated with 20 mM Tris-HCl pH 7.5, 5 mM EDTA, 600 mM NaCl. The column was washed with the same buffer until the absorbance at 280 nm returned to baseline levels. The protein was eluted with 20 mM Tris-HCl pH 7.5, 5 mM EDTA, 2 M NaCl.

The bFGF(MAGS) thus obtained was subjected to N-terminal amino acid sequencing by the Edman degradation technique using an automated gas phase sequenator. When large amounts of protein were loaded onto the sequenator, very small quantities, i.e. 1–2%, of protein having the N-terminal sequence Gly-Ser- were detectable, the remainder of the protein having the N-terminal sequence Ala-Gly-Ser. When bFGF was produced and purified in essentially the same manner using *E. coli* B cells transformed with pTsF-9Δβgal, the resulting protein exhibited a mixed N-terminal sequence comprising approximately 70% Ala-Ala-Gly-Ser- and 30% Ala-Gly-Ser-.

We claim:

1. A method for producing a modified form of human basic fibroblast growth actor having a homogeneous N-terminus which comprises expressing, in *E. coli* strain B, a DNA sequence encoding the 155-amino acid precursor form of human basic fibrolast growth factor less one of the two alanine residues immediately following the N-terminal methionine; and recovering the expressed protein without the N-terminal methionine residue.

2. The method of claim 1, wherein the DNA coding sequence that is expressed comprises the coding sequence in FIG. 1A minus the alanine (GCC) codon at bases 7–9.

3. The method of claim 1, wherein the DNA coding sequence that is expressed is the coding sequence in FIG. 2.

4. The method of claim 1, wherein the human basic fibroblast growth factor is expressed at a level of at least 10% of the total protein expressed by the host cell.

5. A vector for the expression of a modified form of human basic fibroblast growth factor having a homogeneous N-terminus, comprising a DNA sequence encoding the 155-amino acid precursor form of known basic fibroblast growth factor less one of the two alanine residues immediately following the N-terminal methionine residue, said DNA sequence being operably linked to a regulatory sequence capable of directing its expression in a host cell.

6. The vector of claim 5, wherein the DNA sequence encoding the growth factor amino acid sequence comprises the coding sequence in FIG. 1A, minus the alanine (GCC) codon at bases 7–9.

7. The vector of claim 5, wherein the DNA sequence encoding the growth factor amino acid sequence comprises the coding sequence in FIG. 2.

8. The vector of claim 5, wherein the regulatory sequence comprises the trp promoter-operator sequence.

9. A host cell which has been transformed with the vector of claim 5.

10. The host cell of claim 9, wherein the cell is an *E. coli* cell.

11. The host cell of claim 10, wherein the host cell is an *E. coli* B cell.

* * * * *